United States Patent
Chenaux et al.

(10) Patent No.: US 10,869,678 B2
(45) Date of Patent: *Dec. 22, 2020

(54) OFFSET REAMER DRIVER

(71) Applicant: Incipio Devices SA, Saint-Blaise (CH)

(72) Inventors: Fabrice Chenaux, Cortaillod (CH); André Lechot, Orvin (CH); Thierry Gentil, Evilard (CH)

(73) Assignee: Incipio Devices SA, St. Blaise (CH)

( * ) Notice: Subject to any disclaimer, the term of this patent is extended or adjusted under 35 U.S.C. 154(b) by 262 days.

This patent is subject to a terminal disclaimer.

(21) Appl. No.: 15/753,336

(22) PCT Filed: Aug. 18, 2016

(86) PCT No.: PCT/IB2016/001143
§ 371 (c)(1),
(2) Date: Feb. 19, 2018

(87) PCT Pub. No.: WO2017/029546
PCT Pub. Date: Feb. 23, 2017

(65) Prior Publication Data
US 2018/0206857 A1    Jul. 26, 2018

Related U.S. Application Data

(60) Provisional application No. 62/206,351, filed on Aug. 18, 2015, provisional application No. 62/256,749, filed on Nov. 18, 2015.

(51) Int. Cl.
*A61B 17/16* (2006.01)
*A61B 50/30* (2016.01)
*A61B 50/33* (2016.01)

(52) U.S. Cl.
CPC ...... *A61B 17/1666* (2013.01); *A61B 17/1624* (2013.01); *A61B 17/1631* (2013.01); *A61B 50/30* (2016.02); *A61B 50/33* (2016.02); *A61B 2050/3008* (2016.02)

(58) Field of Classification Search
CPC .................. A61B 17/1631; A61B 17/1666
See application file for complete search history.

(56) References Cited

U.S. PATENT DOCUMENTS

| 3,740,969 | A | * | 6/1973 | Shotter | F16D 3/41 464/11 |
| 4,037,778 | A | * | 7/1977 | Boyle | B65B 67/1238 141/390 |
| 2003/0216716 | A1 | * | 11/2003 | Desarzens | A61B 17/1666 606/1 |
| 2005/0216022 | A1 | * | 9/2005 | Lechot | A61B 17/1631 606/81 |
| 2008/0058804 | A1 | | 3/2008 | Lechot et al. | |
| 2013/0213678 | A1 | | 8/2013 | Weekes | |
| 2013/0331841 | A1 | | 12/2013 | Roger et al. | |

OTHER PUBLICATIONS

International Search Report, International patent application No. PCT/IB2016/001143, dated Feb. 10, 2017.

* cited by examiner

*Primary Examiner* — Nicholas W Woodall
(74) *Attorney, Agent, or Firm* — Da Vinci Partners LLC; John Moetteli

(57) ABSTRACT

A system, method and/or reamer driver device provides a fully closed tube which prevents the invasion of debris and minimizes abrasion of soft tissue during use. The reamer device includes a minimum number of component assemblies, so as to permit easy replacement and minimize wear.

25 Claims, 34 Drawing Sheets

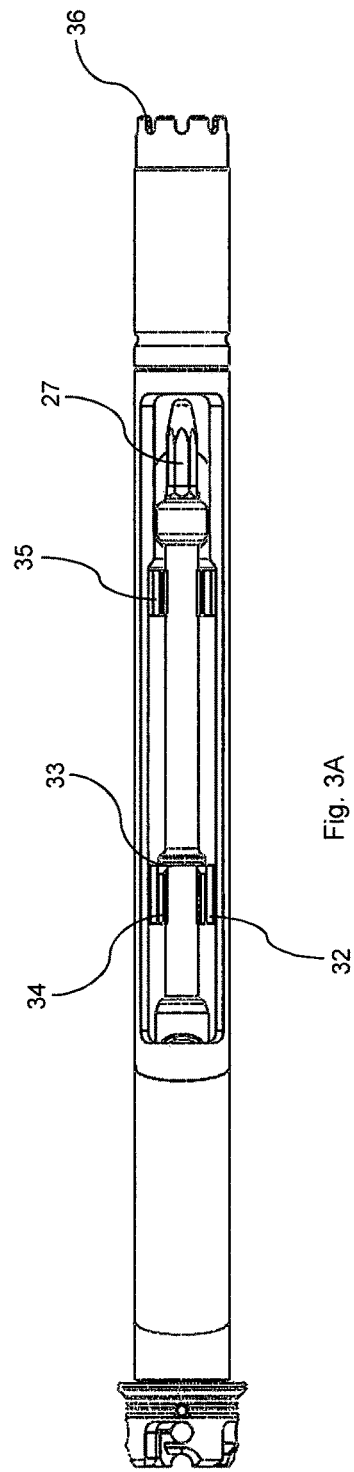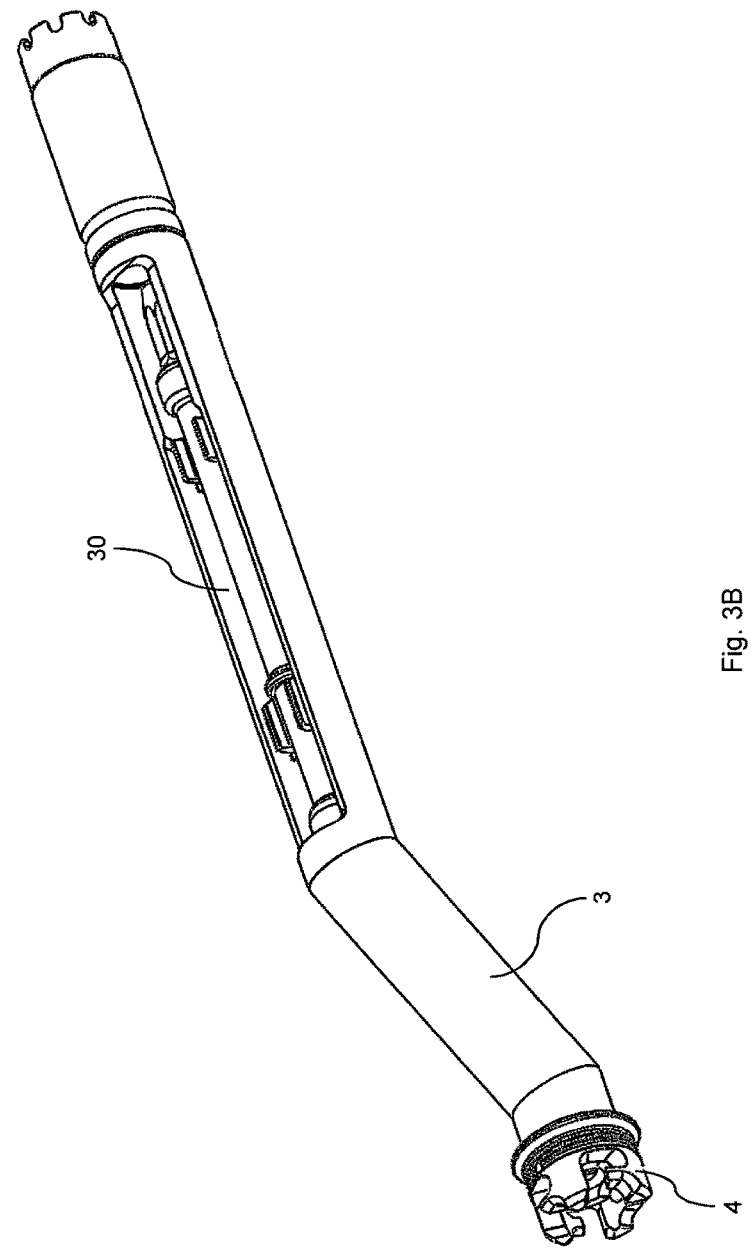

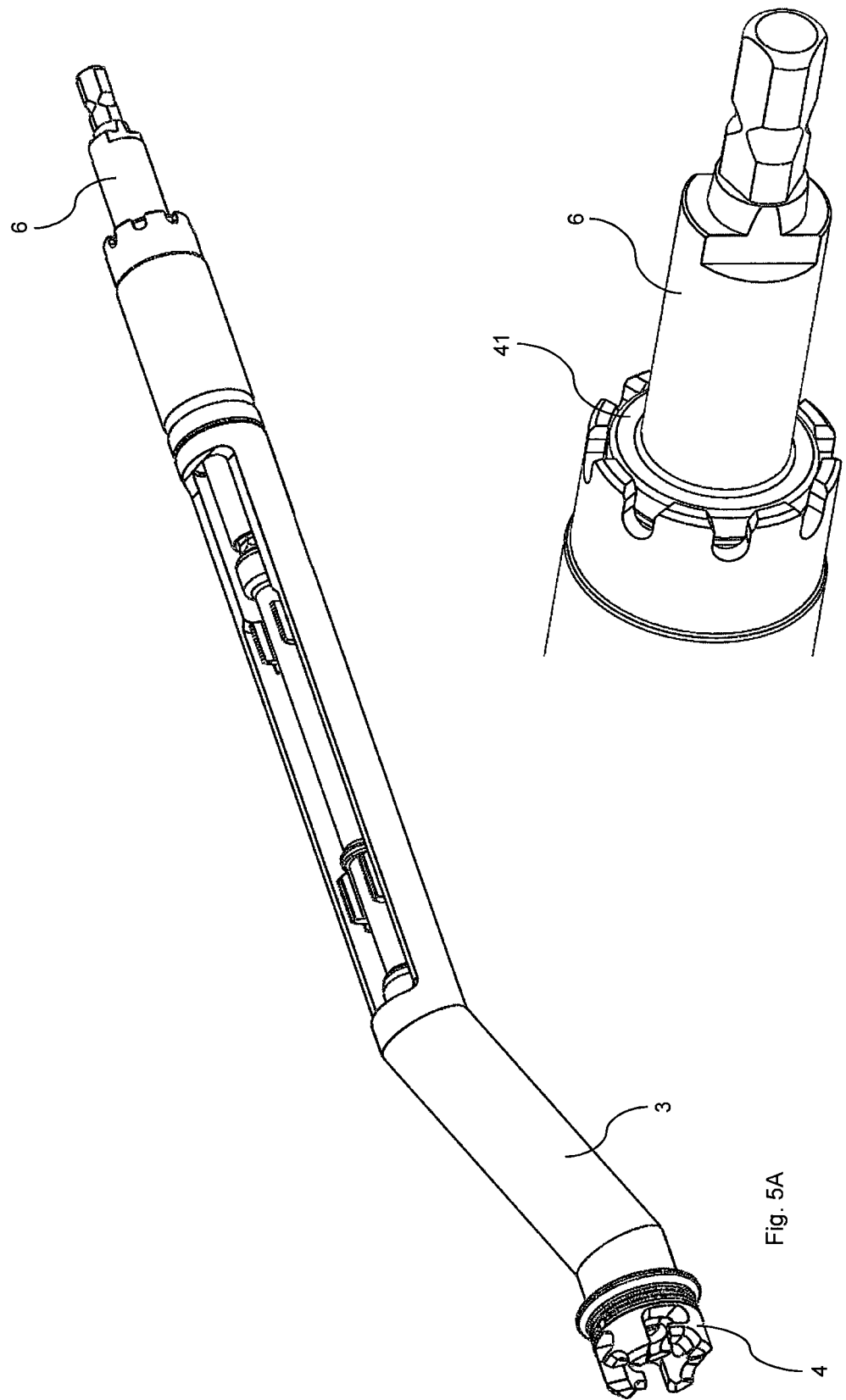

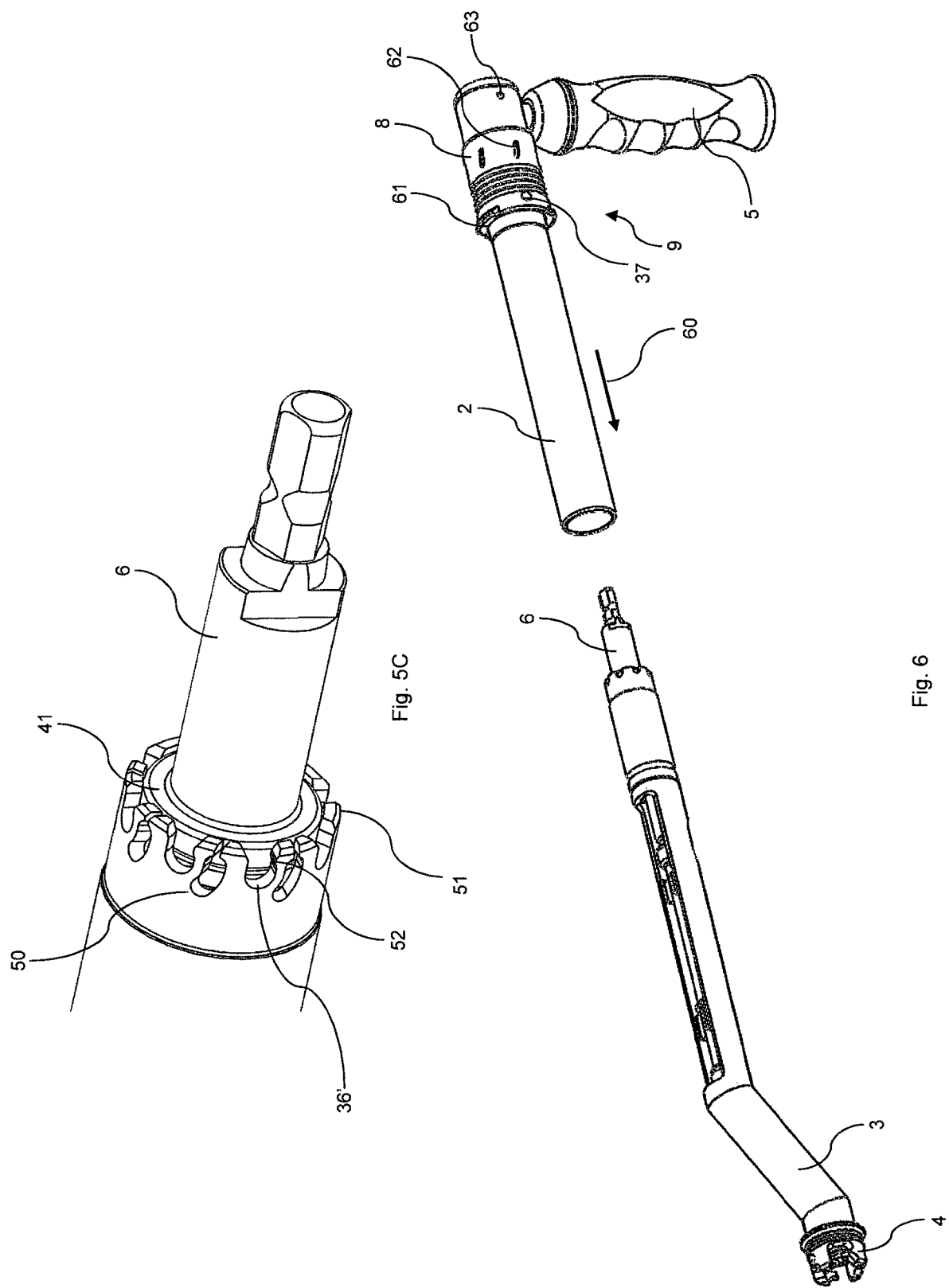

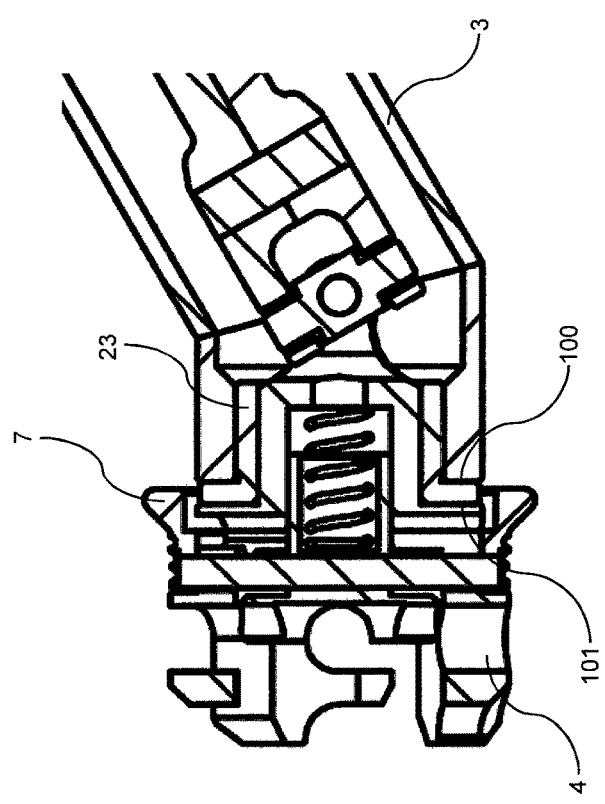
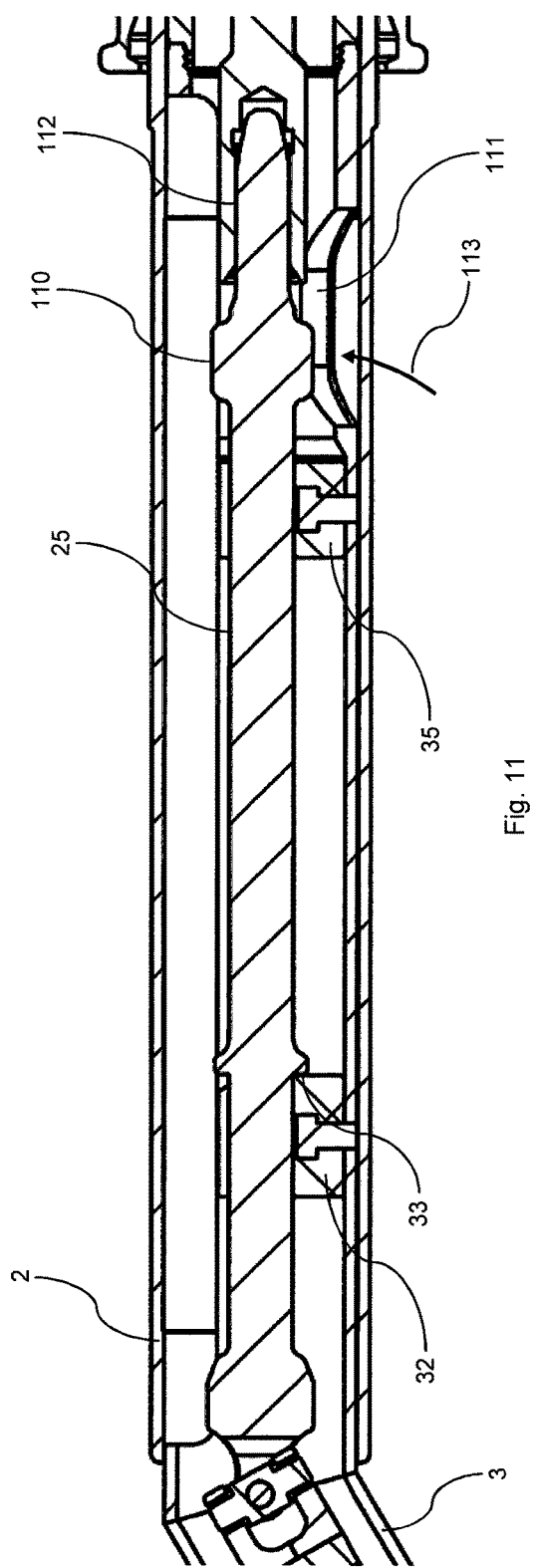
Fig. 10
Fig. 11

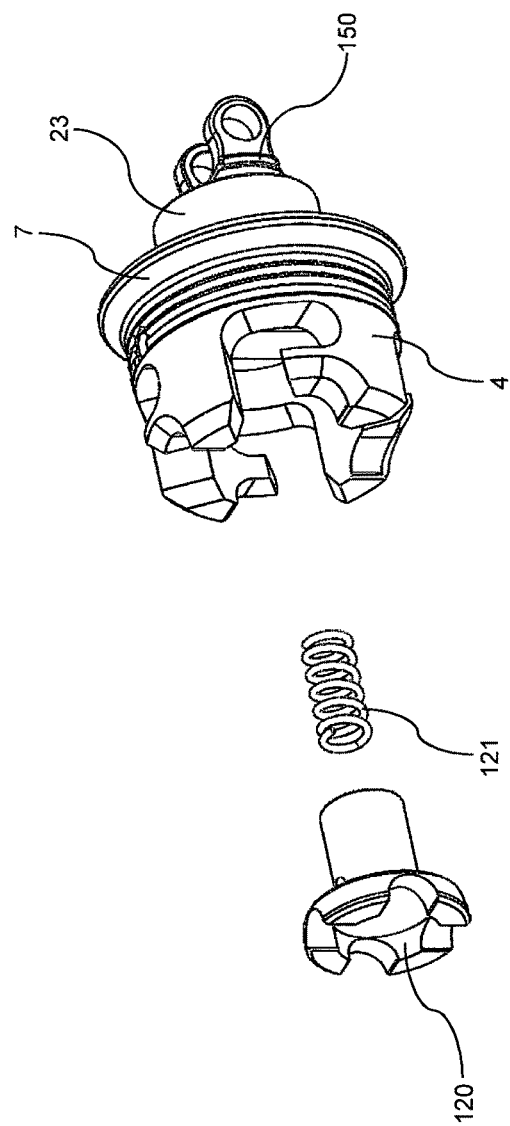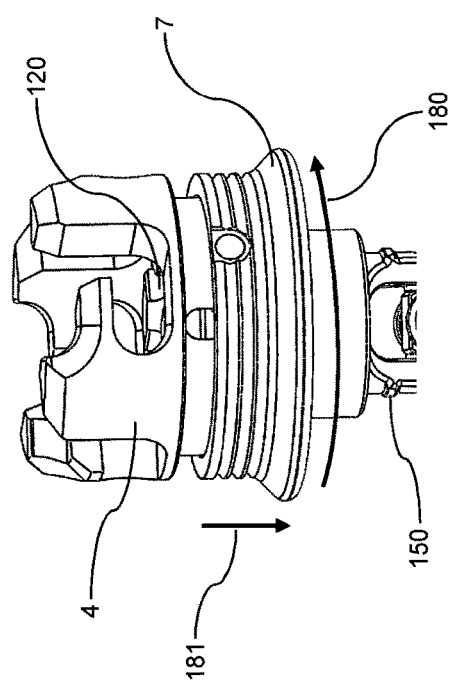

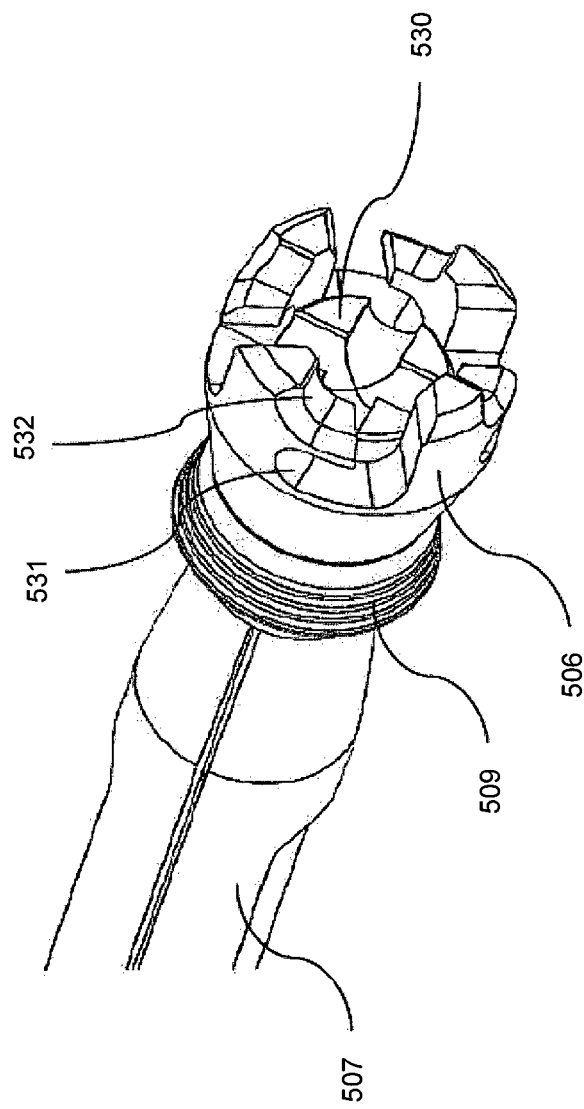

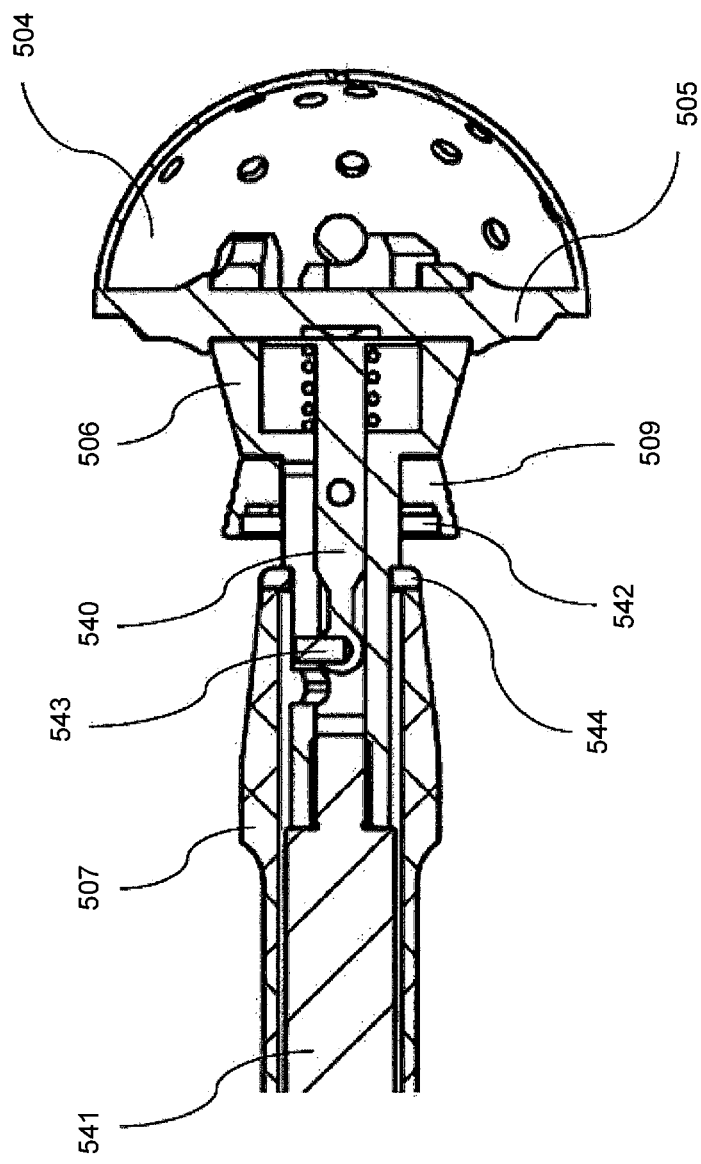

OFFSET REAMER DRIVER

CROSS REFERENCE TO RELATED APPLICATIONS

This application is the National Stage of International Application No. PCT/IB2016/001143, filed Aug. 18, 2016, which claims benefit under 35 USC § 119(a), to U.S. provisional patent application Ser. No. 62/206,351, filed Aug. 18, 2015 and to U.S. provisional patent application Ser. No. 62/256,749, filed Nov. 18, 2015.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

BACKGROUND OF THE INVENTION

This invention relates to a reamer driver suitable constructed to be used to reshape acetabular.

There exists a need for a reamer driver in order to avoid penetration of debris and abrasion of soft tissues into the mechanism of the said reamer driver.

SUMMARY OF THE INVENTION

An improved surgical reamer driver has four basic components and a distal and proximal end. The four components include a housing assembly, a transmission drive train, a motor shaft coupling, and a handle assembly. The transmission drive train is enclosed in the housing assembly, and has a surgical tool connector at the distal end thereof. The motor shaft coupling is disposed at the proximal end thereof. A handle assembly is disposed at the proximal end thereof.

An object of the invention is to provide a driver which, in a fully assembled state, effectively prevents debris from access in the inner workings of the device. This encapsulation of the inner workings also prevents abrasion of soft tissues during use.

Another object of the invention is to provide a driver which allows an easy replacement of components e.g. when components are worn out.

Another object of the invention is to provide a driver wherein the transmission of the load applied on the motor shaft coupling is essentially transmitted to the body of the reamer handle. The load applied on the handle is also essentially transmitted to the body of the reamer handle. There is no contact between the motor shaft coupling and the handle assembly. These two cumulated loads are directly transmitted to the reamer head without compressing the universal transmission drive chain, which transmit the torque applied essentially on the motor shaft coupling.

Another object of the invention is to provide a reamer driver having a simple reamer driver connection that allows quick connect of different type of acetabular reamers from the center of the driver with a mechanism with no nukes or crannies that might trap or attract bone chips or debris. In comparison to the existing reamer driver connections described in the prior art, the locking mechanism located in the center of the driver consists of a plate whose length in the axial direction allows for axial translation without revealing spaces in which debris or chips might enter, thereby preventing such debris and bone chips from jamming the mechanism. Chips and debris is highly undesirable as such may potentially disconnect the reamer from the reamer driver. It also reduces soft tissue irritation while rotating by limiting the sharp edges of components located around the head of the reamer driver.

Another object of the invention is to provide a locking mechanism in the head of a driver which, unlike the standard lock/release function, can be locked in its open position. This allows the surgeon to insert the cutting tool through a minimal invasive opening first. Then, once locked, the reamer handle can be inserted through the same minimal invasive opening and connected to the cutting tool without activating the locking of the mechanism.

BRIEF DESCRIPTION OF THE DRAWINGS

The attached drawings represent, by way of example, different embodiments of the subject of the invention.

FIG. 3A is a top view of the housing assembly of the reamer driver, showing the transmission drive chain assembled.

FIG. 3B is a perspective view of the housing assembly of the reamer driver, showing the transmission drive chain assembled.

FIG. 5A is a perspective view of the housing assembly of the reamer driver, showing a part of the transmission drive chain, and showing the motor shaft coupling coupled to the transmission drive chain.

FIG. 5B is a detail of FIG. 5A showing the motor shaft coupling in the position coupled to the transmission drive chain.

FIG. 5C is a detail showing a snap feature of the invention for retaining the handle against free fall when disassembling the reamer handle.

FIG. 6 is a perspective view of the housing assembly of the reamer driver, showing a part of the transmission drive chain, the motor shaft coupling coupled to the transmission drive chain, and the handle assembly uncoupled to the motor shaft coupling and uncoupled to the housing assembly of the reamer driver.

FIG. 10 is a detail of FIG. 8 showing the reamer head portion.

FIG. 11 is a detail of FIG. 8 showing the transmission drive chain positioned in the body of the reamer driver.

FIG. 17 is a partially exploding view of the reamer head portion.

FIG. 18 is a perspective view of the reamer head connection in the lock open position.

FIG. 24 shows a different view of the reamer driver head.

FIG. 25 shows a cross-section view of the reamer driver head having an acetabular reamer connected to it.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary embodiments disclosed herein without departing from the spirit and scope of the invention.

Figure 1:
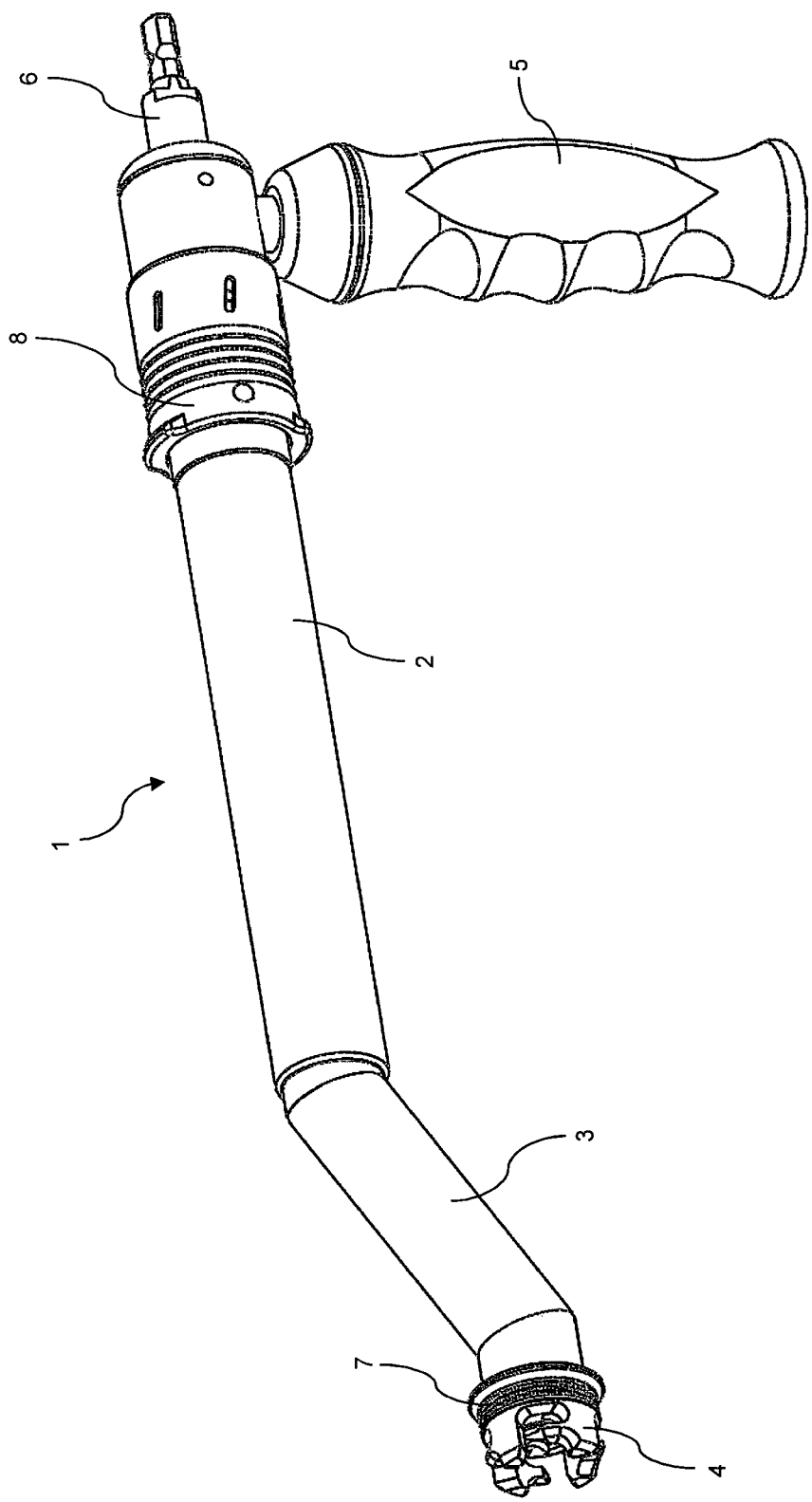
FIG. 1 is a perspective view of the fully assembled reamer driver.

Referring to FIG. 1 showing the assembled reamer driver 1. Such a reamer driver 1 is a surgical instrument used to drive bone cutting tools during minimal invasive surgeries. A distal tube 2 of the handle assembly 9 fully closing the top opening 30 of the body 10. This tube 2 is part of the handle assembly 9. Housing assembly or handle assembly 10 preferably has a Z shape at position 3, where the central axis of the proximal transmission shaft 25 (power input) and the central axis of the distal transmission shaft 24 (power output) are not coincident. A quick tool connector 4, is affixed to the distal transmission shaft 24. Bone cutting tools (not shown) are connected to the said reamer head 4. Handle 5 is part of handle assembly 9. The handle 5 may be for example out of metal, plastic or silicone, and possess an anti-slippery coating, and may be shaped ergonomically, with or without anti-slippery profile. A motor shaft quick connection 6 allows the application of torque. The ring 7 allows the release of a bone cutting tool (not shown). The sleeve 8 allows the release of the handle assembly 9. One of the differences to the known prior art is that the device is the fully encapsulated, avoiding penetration of debris and abrasion of soft tissues during use. The variant shown in the figures is made out of four main components, the transmission drive chain 21, the body 10, the motor shaft coupling 11 and the handle assembly 9.

Figure 2:
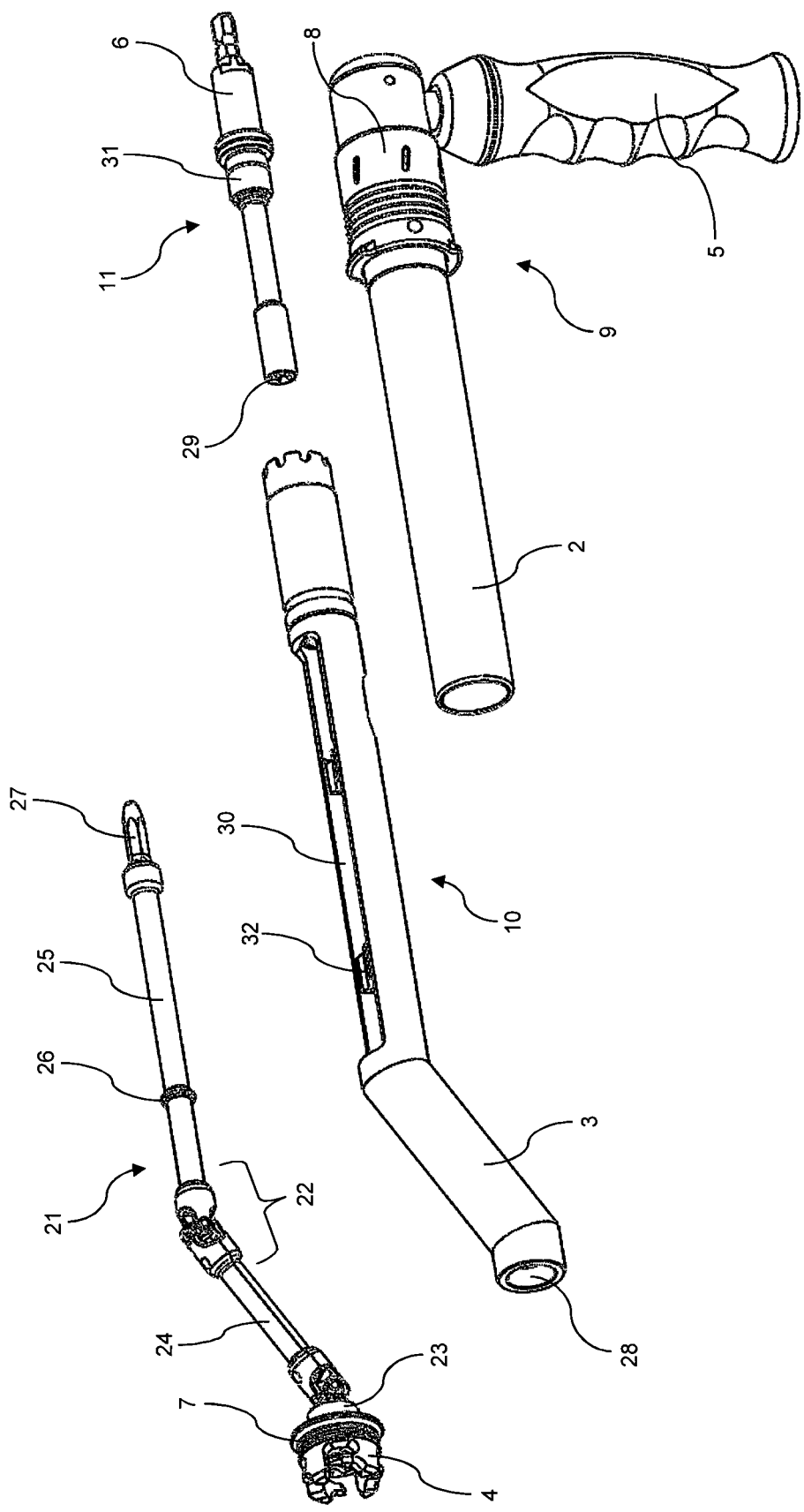
FIG. 2 is an exploding view of main components of the reamer driver.

Now referring to FIG. 2 showing the main components, the transmission drive chain 21, the body 10, the motor shaft coupling 11 and the handle assembly 9, separated from each other. Mechanical load applied on the handle 5 is transmitted through to the head bearing 23 and finally to the driver head 4. There is no transmission of load into the motor shaft coupling 11. The head bearing 23 may be made for example out of PEEK, carbon fiber PEEK, Teflon, PPSU, metal. The transmission drive chain typically includes universal joints 22, a distal transmission shaft 24, a proximal transmission shaft 25, a stop ring 26 allowing the axially positioning of the transmission drive chain when inserted into the bearing (s) 32, 35, a rotational transmission feature 27 (Hex, square, triangle, . . . ) allowing transmission of the rotational torque from the motor shaft coupling 11 to the transmission drive chain 21. This feature transmits only rotational torque but not the eventual axial force applied on the motor shaft coupling 11. A front opening 28 of the housing assembly 10 where the transmission drive chain 21 can be inserted. A rotational transmission feature 29 (Hexagon, square, triangular, or any polygonal shape) to be connected with rotational transmission feature 27. A top opening 30 of the housing assembly 10 where the transmission drive chain 21 exits during while inserting into the housing assembly 10 and before it reaches its assembled position. Motor shaft bearing 31 may be made for example out of PEEK, carbon fiber PEEK, Teflon, PPSU or metal. One or more distal transmission drive chain bearing(s) 32, 35, may be made for example out of PEEK, carbon fiber PEEK, Teflon, PPSU or metal, having a snapping feature to capture the proximal transmission shaft 25 and maintain it in place. This distal transmission drive chain bearing(s) 32, 35 are also insuring the axial positioning of the transmission drive chain with the stop ring 26.

Figure 7B:
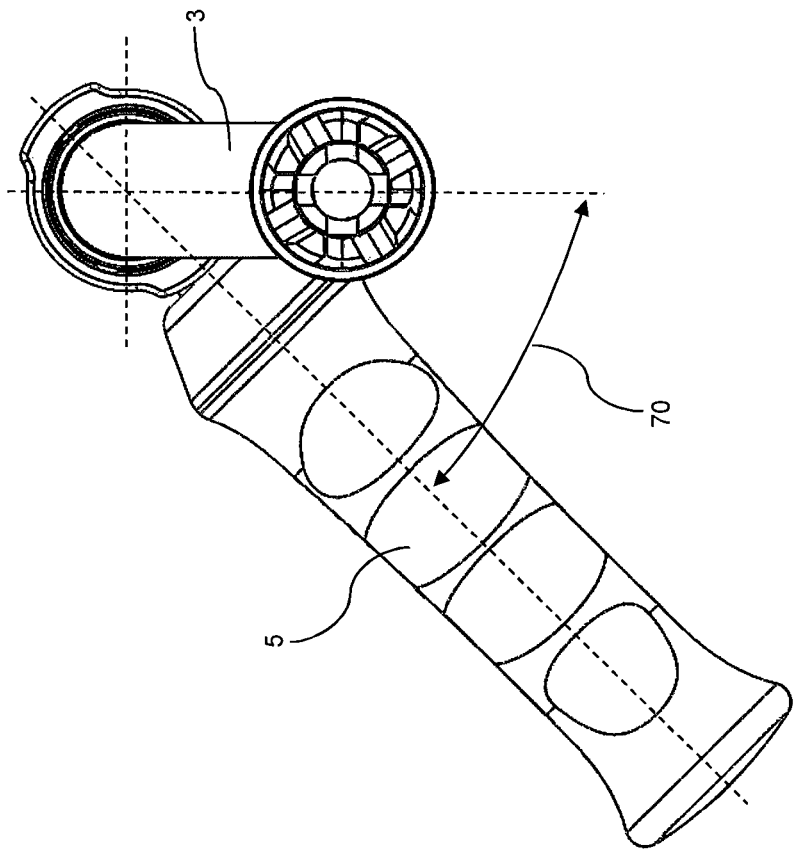
FIG. 7B is a front view of the assembled reamer driver with the handle indexed in an angled position.
Figure 7A:
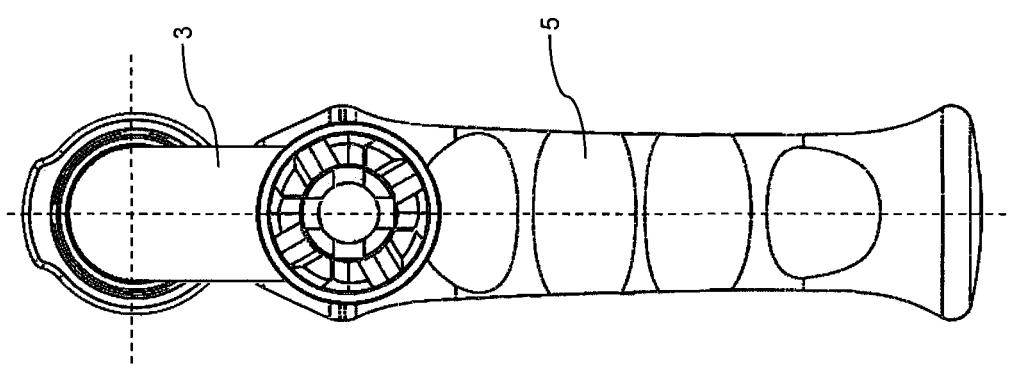
FIG. 7A is a front view of the assembled reamer driver with the handle indexed in the vertical position.

Now referring to FIG. 3A and FIG. 3B, whereof FIG. 3A is showing a top view of the housing assembly 10 of the reamer driver 1, showing the transmission drive chain 21 assembled and FIG. 3B is showing a perspective view of the housing assembly 10 of the reamer driver 1, showing the transmission drive chain assembled. A point of contact 33 between the stop ring 26 and the distal transmission drive chain bearing(s) 32, 35 is avoiding axial frontward movement of the shaft 25. A point of contact 34 between the proximal transmission shaft 25 and the distal transmission drive chain bearing(s) 32, 35 insures the concentricity of the proximal transmission shaft 25 within the housing (e.g. tubes) of the housing assembly 10 and allows its rotation. Grooves 36 allowing the angular indexing of the handle in several positions, as shown in FIG. 7A and FIG. 7B.

Figure 4:
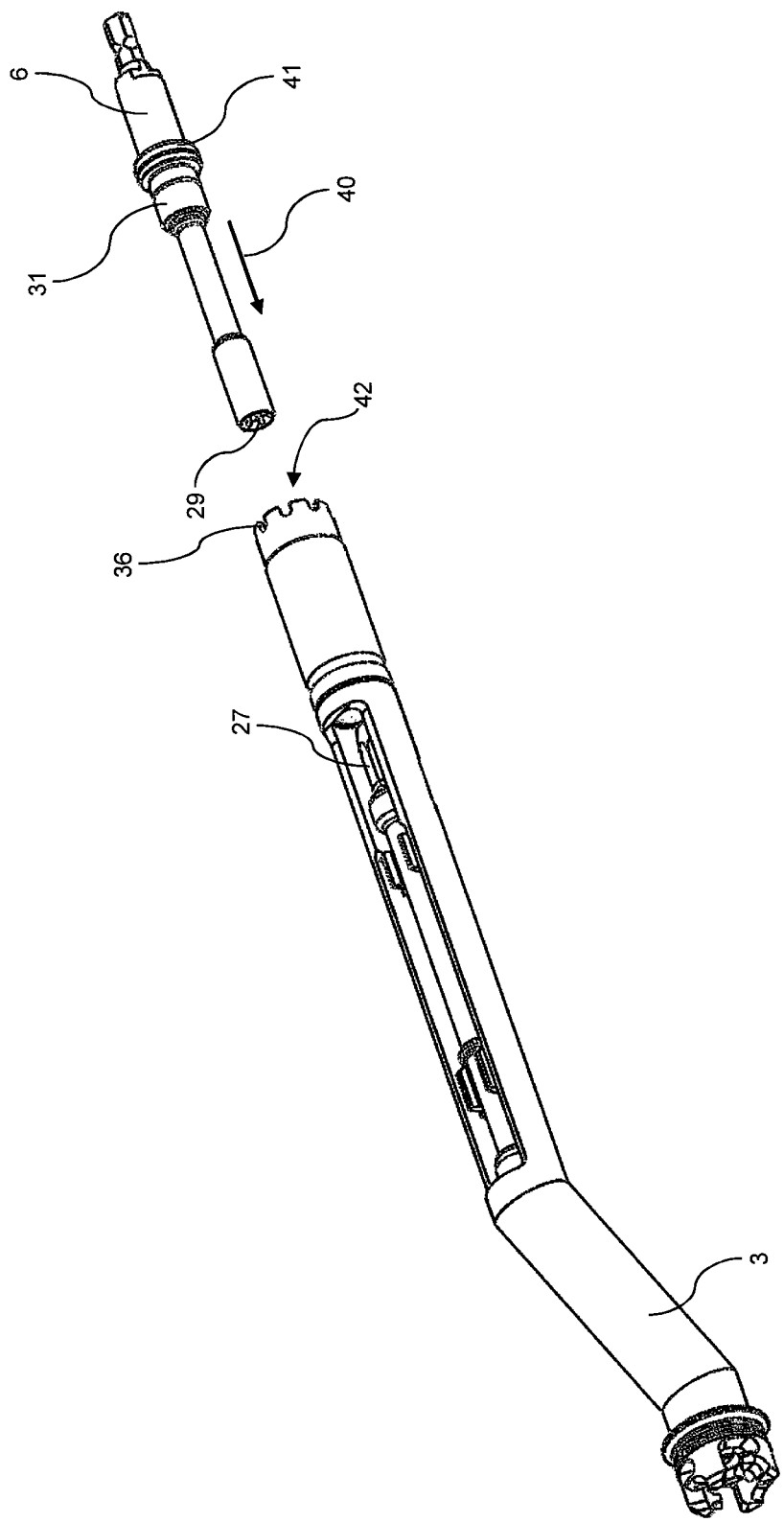
FIG. 4 is a perspective view of the housing assembly of the reamer driver, showing a part of the transmission drive chain, and showing the motor shaft coupling uncoupled from the transmission drive chain.

Now referring to FIG. 4 showing a perspective view of the housing assembly 10 of the reamer driver 1, showing a part of the transmission drive chain 21, and showing the motor shaft coupling 11 uncoupled from the transmission drive chain 21. Insertion of the motor shaft coupling 11 in direction 40 into the housing assembly 10. A retaining ring 41 allowing transmission of the axial load on the motor shaft quick connection 6 onto the motor shaft bearing 31. A back opening 42 of the housing assembly 10 where the motor shaft coupling 11 is being inserted.

Now referring FIG. 5A showing a perspective view of the housing assembly 10 of the reamer driver 1, showing a part of the transmission drive chain 21, and showing the motor shaft coupling 11 coupled to the transmission drive chain 21.

Now referring FIG. 5B showing a detail of FIG. 5A, showing the motor shaft coupling 11 in the position coupled to the transmission drive chain. Whereas the transmission of the load 96 applied on the motor shaft coupling 11 is made through the retaining ring 41 to the motor shaft bearing 31 and finally to the housing assembly 10. No load is transmitted into the handle assembly 9. There is no contact between the motor shaft coupling 11 and the handle assembly 9.

Referring now to FIG. 5C, a snap feature of the invention for retaining the handle 5 against free fall or inadvertent release when disassembling the reamer handle. The snap feature is enabled by creating a flexible finger retention via, for example, an adjacent relief slot 50 to pin recesses 36', which enables a raised boss 52 on a finger 51 created by this adjacent slot, to move out of the way of a pin 63, and snap back thereby retaining the handle.

Now referring to FIG. 6 showing a perspective view of the housing assembly 10 of the reamer driver 1, showing a part of the transmission drive chain 21, the motor shaft coupling 11 coupled to the transmission drive chain 21, and the handle assembly 9 uncoupled to the motor shaft coupling 11 and uncoupled to the housing assembly 10 of the reamer driver 1. Insertion of the handle assembly 9 in direction 60 onto the assembled body 10, transmission drive chain 21 and motor shaft coupling 11. A trigger feature 61 of the sleeve 8 allowing release of the handle assembly 9. This trigger feature 61 can be made longer in order to be activated by e.g. a finger without moving the hand away from the handle 5 (similar a trigger of a pistol). One or more openings 62 into the sleeve 8 allowing circulation of water/steam during cleaning and sterilization.

Now referring to FIG. 7A and FIG. 7B, whereof FIG. 7A showing a front view of the assembled reamer driver 1 with the handle 5 indexed in the vertical position and whereof FIG. 7B showing a front view of the assembled reamer driver 1 with the handle 5 indexed in an angled position, the indexing angle 70. At least a pin 63 (shown in FIG. 6) located in the handle assembly 9 form-locks with at least one of the grooves 36 and allows the angular indexing of the handle 5 in multiple positions.

Figure 8:
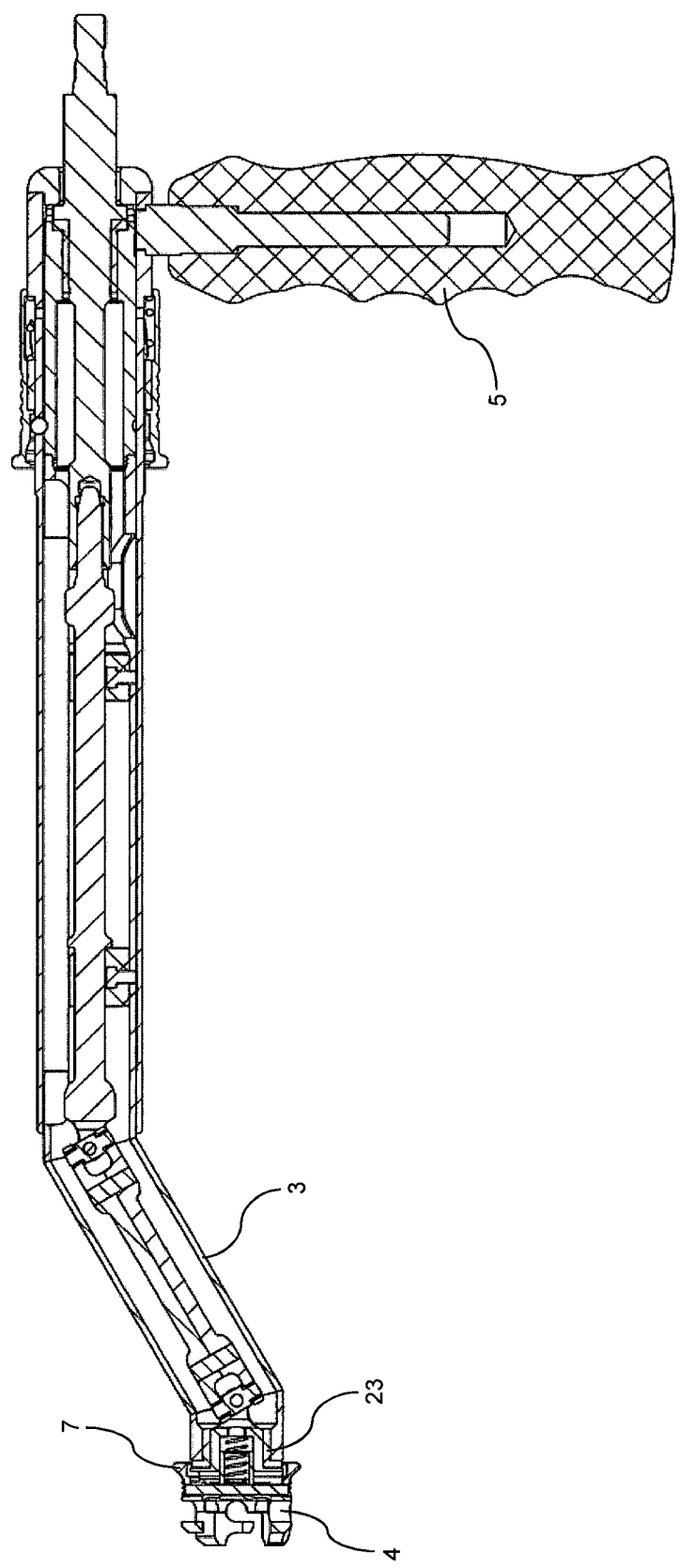
FIG. 8 is a cross-section of the fully assembled reamer driver.

Now referring to FIG. 8 showing a cross-section of the fully assembled reamer driver 1.

Figure 9:
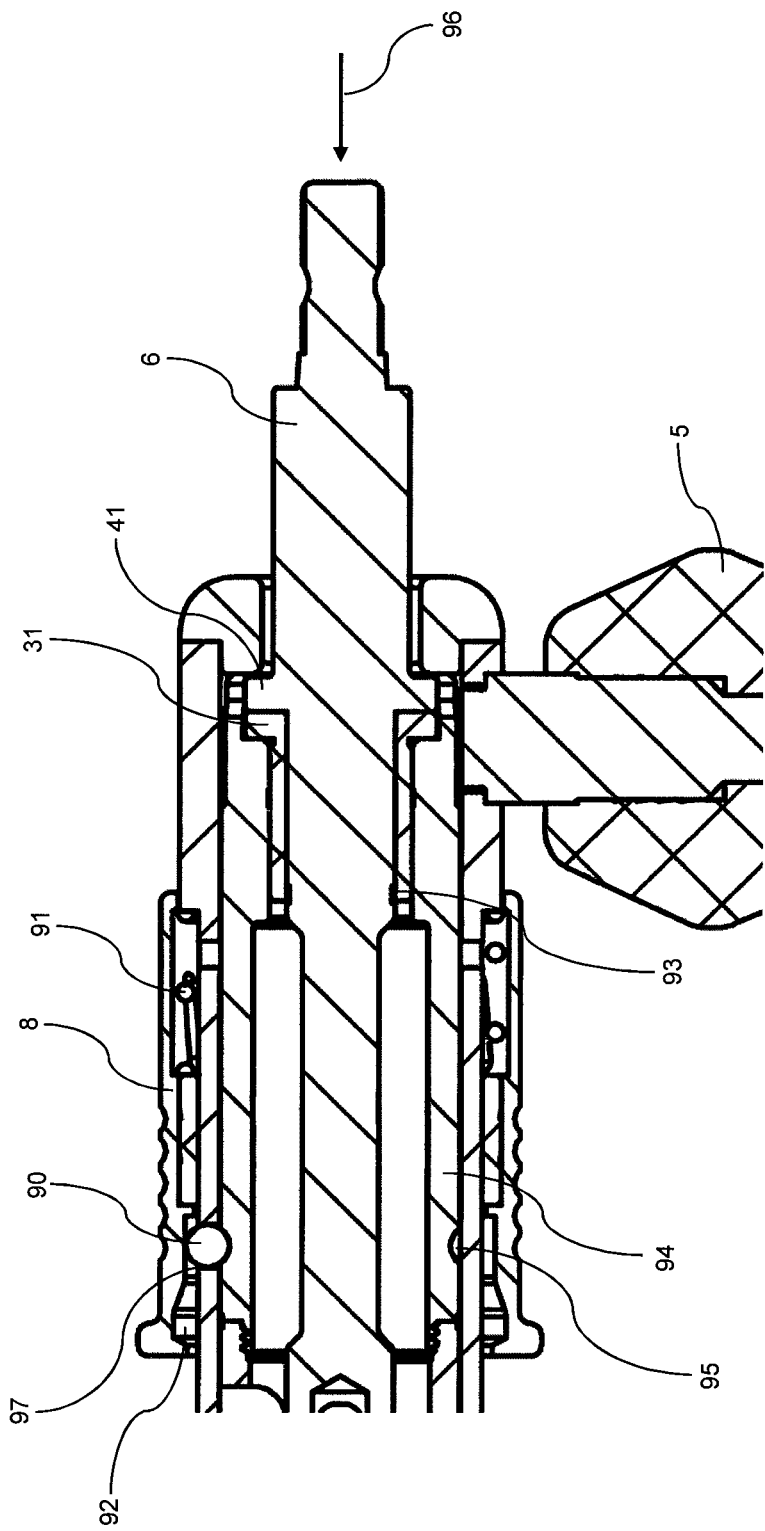
FIG. 9 is a detail of FIG. 8 showing interconnection between the handle assembly, the housing assembly, the motor shaft coupling and the transmission drive chain.

Now referring to FIG. 9 showing a detail of FIG. 8 showing interconnection between the handle assembly 9, the housing assembly 10, the motor shaft coupling 11 and the transmission drive chain 21. A ball 90 allowing connection of the handle assembly 9 with the housing assembly 10. The at least one ball 90, pushed down by profiled groove 92 of the release sleeve 8, falls into the groove 95.

A spring 91 maintaining the release sleeve 8 in its frontward position. The profiled groove 92 allowing the ball 90 to move away from the groove 95 when the release sleeve 8 is in its backward position and allowing the ball 90 to be pushed into the groove 95 when the release sleeve 8 is in its frontward position in order to lock the handle assembly 9 into the housing assembly 10. A groove 93 on the motor shaft coupling 11 where the lip of the motor shaft bearing 31, slightly smaller in diameter, falls into in order to secure the assembly of the motor shaft bearing 31 onto the motor shaft coupling 11. The groove 95 is formed into the proximal portion 94 of the housing assembly 10. One or more hole(s) 97 are formed through the distal tube 2 where they receive the locking ball(s) 90. The inside edge of the hole(s) 97 (towards the inside of the distal tube 2) has a lip slightly smaller diameter than the hole(s) 97 in order to retain the ball(s) 90 of going out.

Now referring to FIG. 10 showing a detail of FIG. 8, showing a point of contact 100 between the distal end of the body 3 and the head bearing 23. An axial load applied on the housing assembly 10 (through the handle assembly 9 and through the motor connection shaft 11) is transmitted to the reamer driver head 4 through the head bearing 23. Further FIG. 8 shows a point of contact 101 between the head bearing 23 and the reamer driver head 4.

Now referring to FIG. 11 showing another detail of FIG. 8, showing an enlarged diameter portion 110 of the proximal transmission shaft 25, increasing the surface of contact when pushing the proximal transmission shaft 25 up for disassembling. A distal opening 111 in the housing assembly 3 allowing access with a finger to push the enlarged diameter portion 110 of the proximal transmission shaft 25 up. A point of contact 112 of the rotational transmission feature 27 allowing transmission of the rotational torque from the motor shaft coupling 11 to the transmission drive chain 21. This feature transmits only rotational torque but not the eventual axial force applied on the motor shaft coupling 11. An access 113 with a finger or other mean to push the proximal transmission shaft 25 up.

Figure 12:
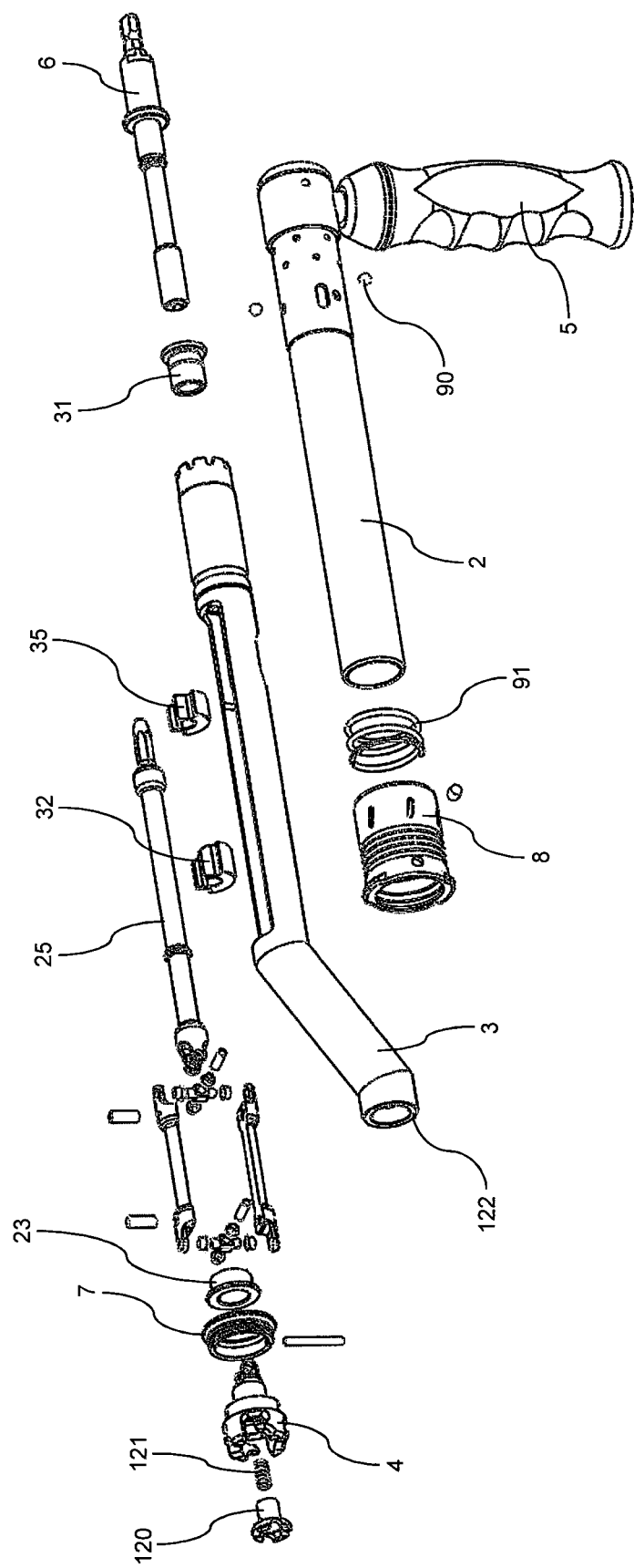
FIG. 12 is a detailed exploding view of individual components used in a variant of the invention.

Now referring to FIG. 12 showing a detailed exploding view of individual components used in a variant of the invention. A central cutting tool connection 120, a spring 121, a front face 122 of the housing assembly 10, transmitting the axial load applied on the housing assembly 10 (through the handle assembly 9 and through the motor connection shaft 11) to the reamer driver head 4 through the head bearing 23.

Figure 13:
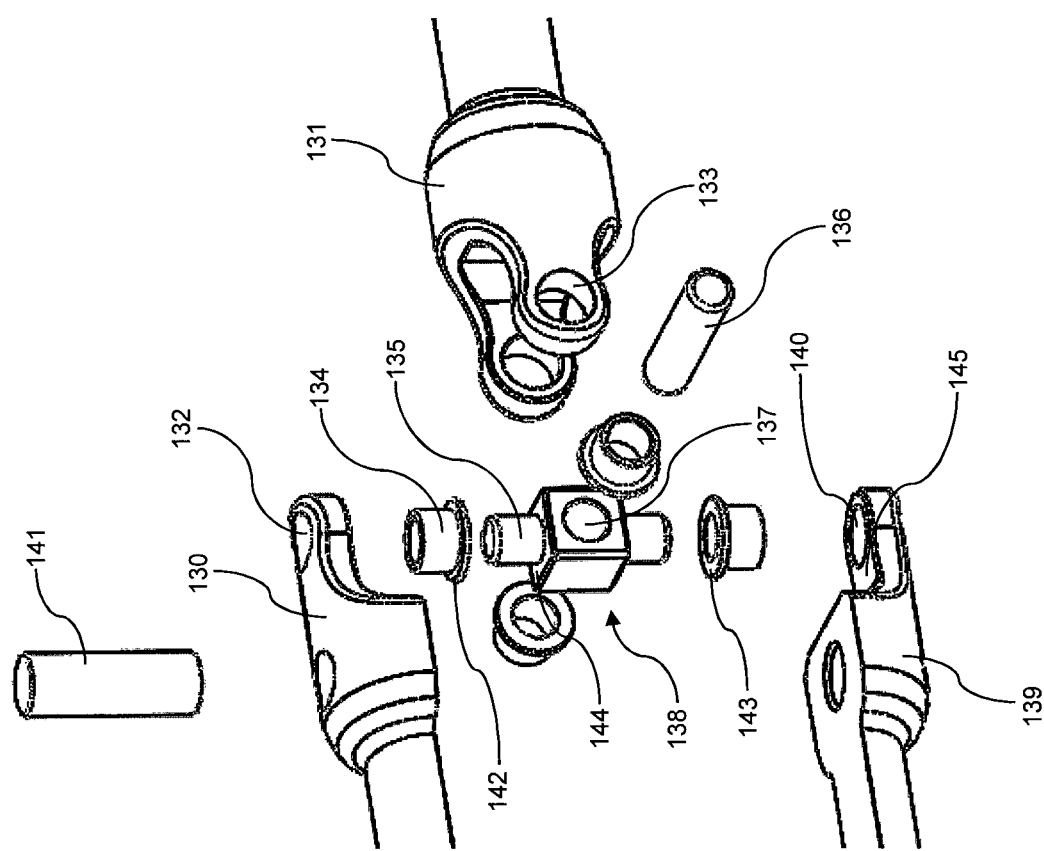
FIG. 13 is a detailed exploding view of typical components used on a universal joint as used as functional element(s) of the transmission drive chain.

Now referring to FIG. 13 showing a detailed exploding view of typical components used on a universal joint 22 as used as functional element(s) of the transmission drive chain 21. A first half 130 and a second half 139 of the first fork of the universal joint 22. The first fork is split in half 130, 139 to allow assembling of the central block 138. A second fork 131 of the universal joint 22. A bearing surface 132 of the first half of the first fork 130. A bearing surface 133 of the second fork 131. Bearing sleeves 134, the bearing sleeve 134 might be made for example out of PEEK, carbon fiber PEEK, Teflon, PPSU or metal. Cylindrical extensions 135 of the central block 138 allowing its rotation with the two halves 130, 139 of the first fork. A cylindrical pin 136 allowing rotation of central block 138 with the second fork 131. The cylindrical pin 136 is press fit into the central hole 137 of the central block 138. A central hole 137 of the central block 138. Bearing surface 140 of the second half 139 of the first fork. A positioning pin 141, press fit into the two halves 130, 139 of the first fork, to maintain the two halves 130, 139 together. Inner bearing surfaces 142 of the bearing sleeves 134 insuring positioning and low friction with the inner surfaces 145 of the fork. Outer bearing surfaces 143 of the bearing sleeves 134 insuring positioning and low friction with the side surfaces 144 of the central block 138. Side surfaces 144 of the central block 138, adjacent to the cylindrical extension 135. Part of the invention is the use of universal joints 22 having four bearing sleeves 134 for this kind of devices. It is expected to highly increase the life of the universal joint 22 by reducing the friction and therefore the wear. More traditional universal joints have metal on metal friction.

Figure 14:
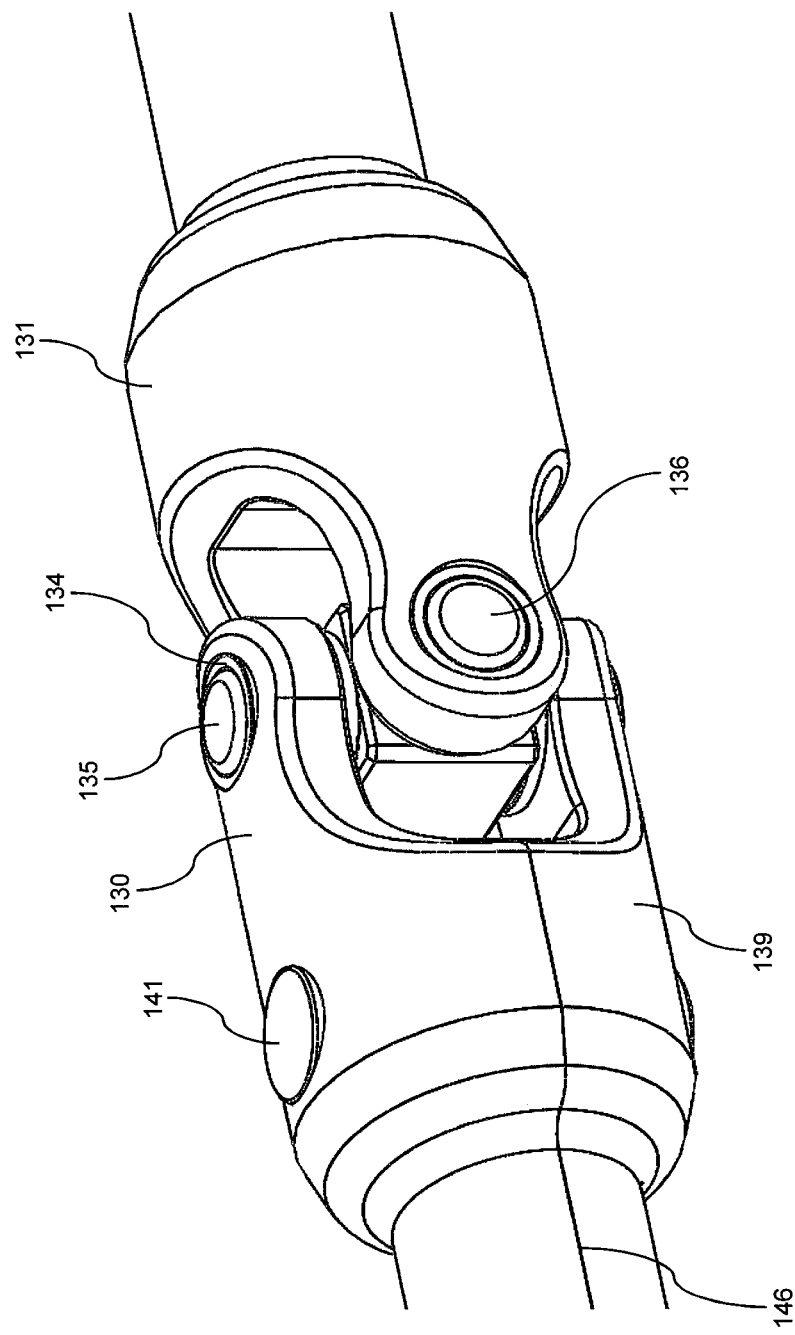
FIG. 14 is a perspective view of a universal joint as used as functional element(s) of the transmission drive chain.

Now referring to FIG. 14 showing a perspective view of a universal joint 22 as used as functional element(s) of the transmission drive chain 21. A contact surface 146 between the two halves 130, 139 of the first fork. In addition to the pin 141, the two halves can be secured together by welding, gluing.

Figure 15:
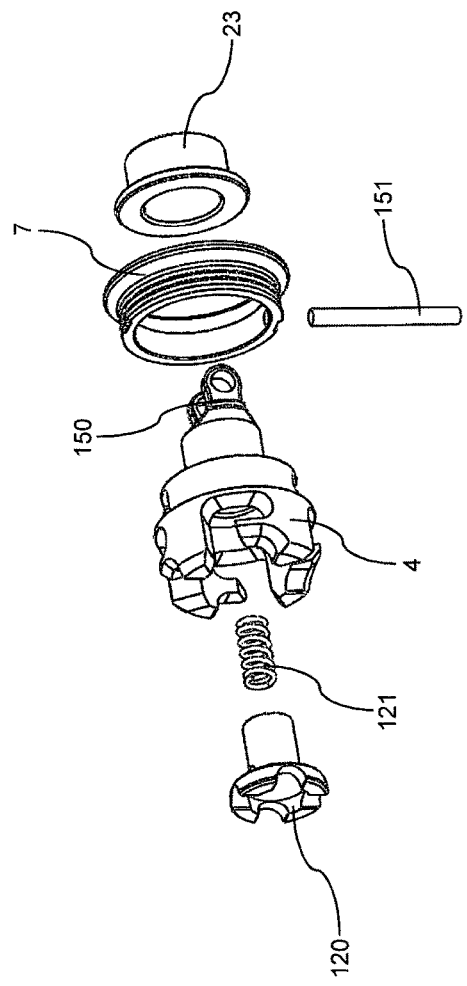
FIG. 15 is a detailed exploding view of the reamer head portion.

Now referring to FIG. 15 showing a detailed exploding view of the reamer head portion. A retaining rib 150 allowing the retention of the head bearing 23 once assembled onto the reamer head 4. This retaining rib 150 is positioned in such way to allow slight translation movement of the head bearing 23 for easier cleaning but to retain the head bearing 23 of falling off. A pin 151 connecting the ring 7 with the central cutting tool connection 120 together, as also visible in FIG. 10.

Figure 16:
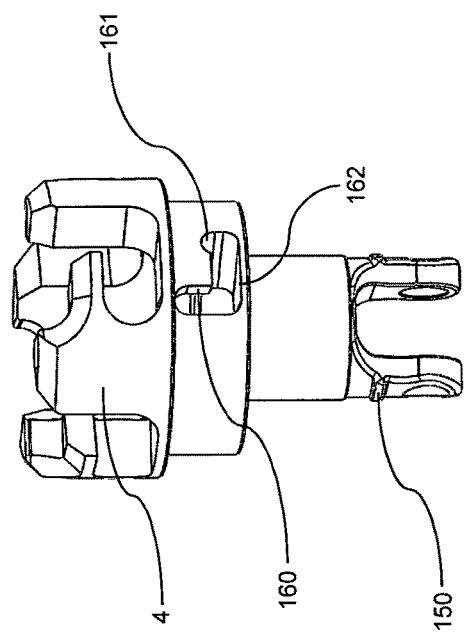
FIG. 16 is a perspective view of the reamer head portion.

Now referring to FIG. 16 showing a perspective view of the reamer head portion. An elongated groove 160 allowing the cutting tool locking mechanism (ring 7, pin 151 and central cutting tool connection 120) to slide backward/frontward in direction 181 in order to release/lock the cutting tool. The cutting tool locking mechanism is spring loaded with spring 121 in its locked position. The elongated groove 161 allowing the cutting tool locking mechanism (ring 7, pin 151 and central cutting tool connection 120) to be locked in the release (open) position. A channel 162 allowing the cutting tool locking mechanism (ring 7, pin 151 and central cutting tool connection 120) to be switched between the release/lock movement and the locked open position by rotation 180.

Now referring to FIG. 17 showing a partially exploding view of the reamer head portion. A central cutting tool connection 120, a spring 121, a reamer head 4.

Now referring to FIG. 18 showing a perspective view of the reamer head connection in the lock open position, indicating the direction 180 of the rotation of the ring 7 (and therefore the tool locking mechanism) to switch between the release/lock movement and the locked open position. Indicating the direction 181 of a pull movement of the ring 7 (and therefore the tool locking mechanism) to release the cutting tool.

Figure 19:
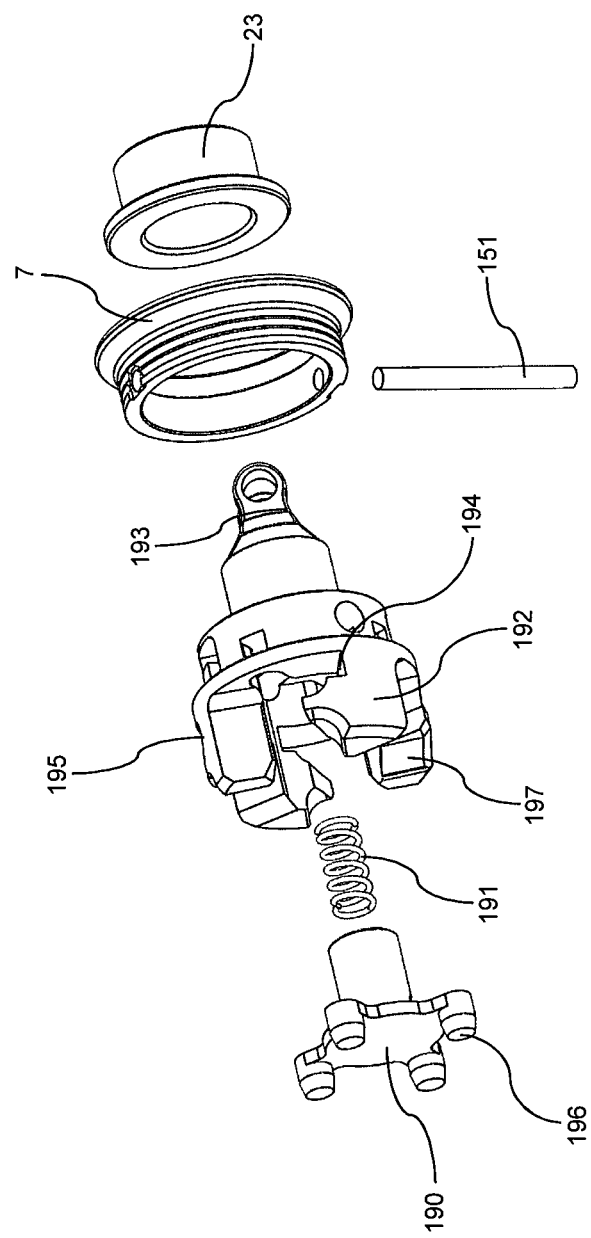
FIG. 19 is a multiple reamer coupling of the invention is shown.
Figure 20:
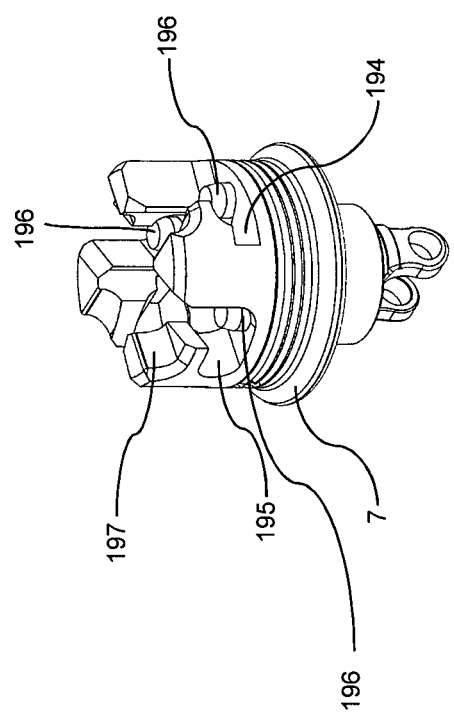
FIG. 20 is a multiple reamer coupling of the invention is shown.

Referring now to FIGS. 19 and 20, an alternate multiple reamer coupling of the invention, used to connect with the reamer bar 211 shown in FIG. 30, has a locking head 190 with at least one pin 196 located in such a way as to close the L-shaped openings 195 and therefore capture the connecting bars of the acetabular reamer once engaged into it in order to maintaining the reamer firmly connected to the driver. Different L-shaped openings 194 may be used to connect non-cylindrical connecting bars of different types of acetabular reamers. As shown is these figures, both rectangular L-shaped openings 194 and cylindrical L-shaped openings 195 are used in the same reamer head in order to connect different acetabular reamers having either rectangular or cylindrical connecting bars.

A further alternate embodiment of the multiple reamer coupling of the invention has strategically located pins 196 lock the cutting tool in place.

Figure 21:
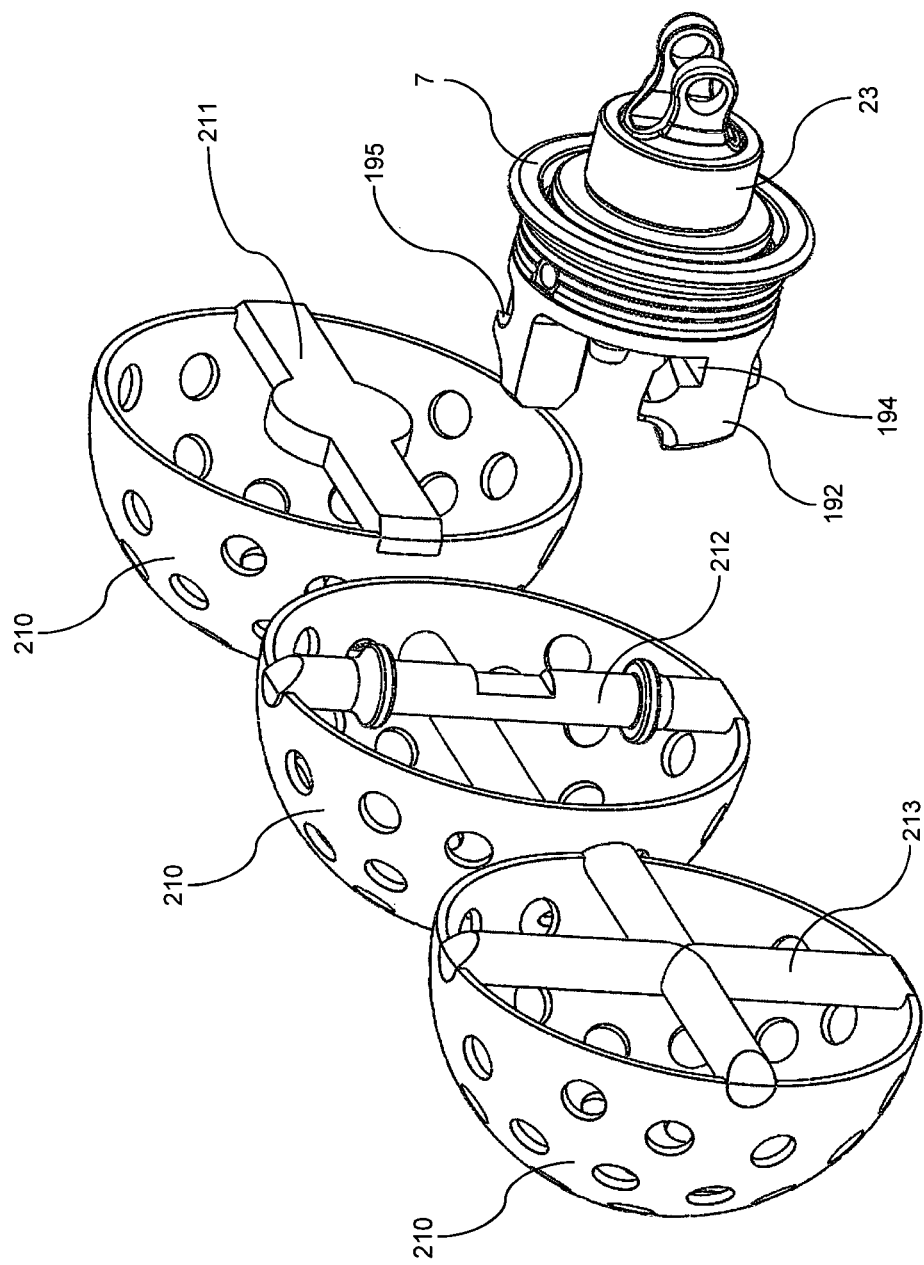
FIG. 21—is a multiple reamer coupling of the invention is shown.

Referring now to FIG. 21, the embodiment of FIG. 20 may be configured, based on the location of the locking pins, to lock three different types of tools 210, having three different types of interfaces 211, 212, and 213, respectively.

Figure 22:
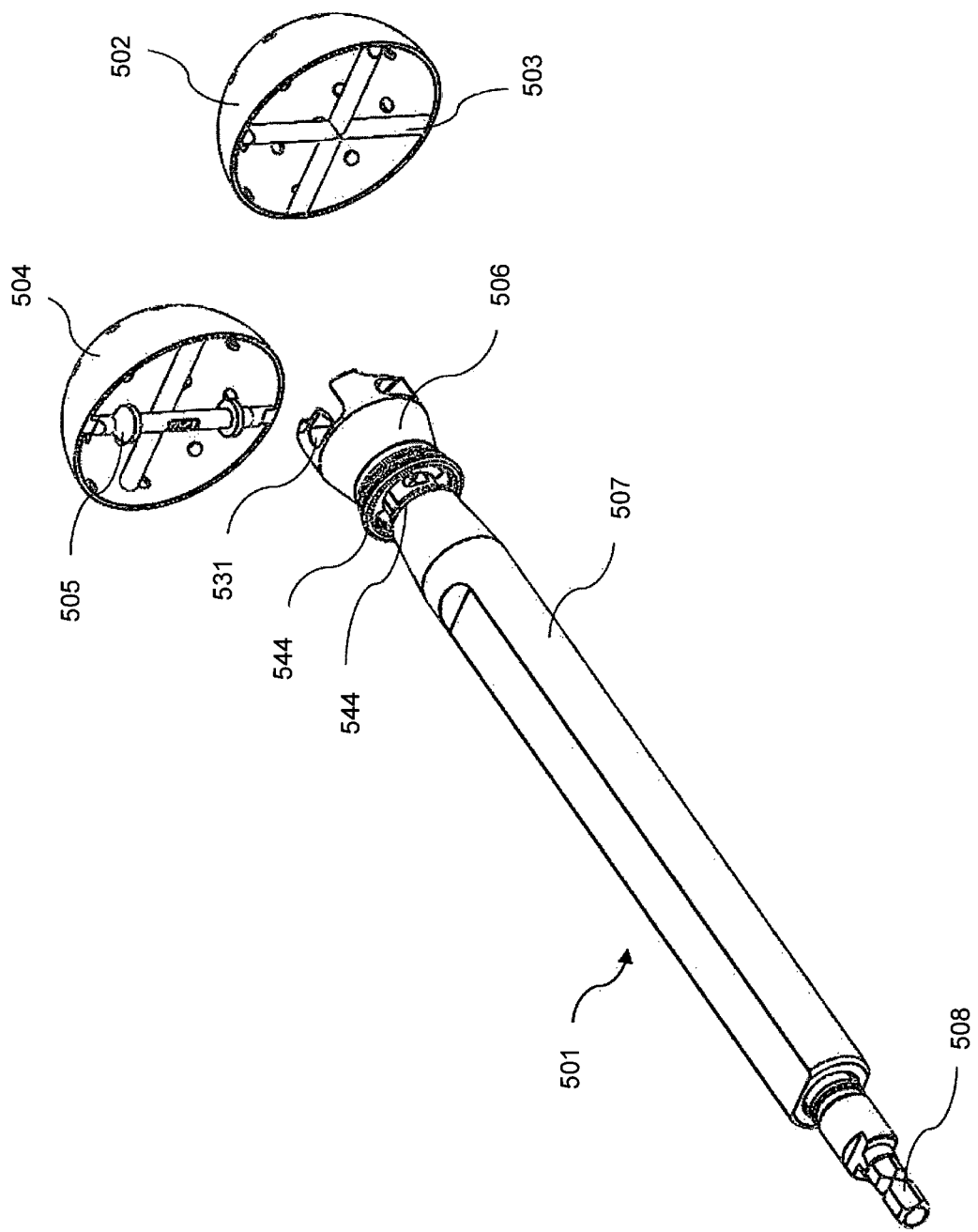
FIG. 22 shows a perspective view of the preferred embodiment of the reamer driver with two acetabular reamers with different type of couplings.

Referring to FIG. 22, an acetabular reamer driver 501 is provided to assist the surgeon in reaming the acetabular socket for the implantation of a cup prosthesis. The reamer driver 501 comprises a driver head 506 that can be connected to different types of acetabular reamers. A release sleeve 509 can be pulled backward to open the connection and connect or release the acetabular reamer from the driver. The driver head 506 has an elongated shaft 541 ending by a quick connector 508 that can be coupled to a source of energy (powered drill as example). A handle sleeve 507 is assembled around the elongated shaft 541 and allows the surgeon to hold the reamer driver while rotating. A washer 544 insures bearing contact between the handle sleeve 507 and the distal portion of the reamer driver.

By way of example only, two acetabular reamers with different type of couplings are shown. The acetabular reamer 502 has four connecting bars 503 converging at the center of the reamer to form a cross. The acetabular reamer 504 has two connecting bars 505 spaced apart and perpendicular from each other. It will be noted that the acetabular reamer connections may have only 2 or 3 connecting bars not necessary oriented perpendicular to each other. The acetabular reamer may be of different shapes, like cylindrical, conical, flat or any other profile. Different instruments than acetabular reamers may be connected to the reamer drive. The shape of the bars 503 and 505 has a circular cross-section but can be of any other shape or cross-section.

Figure 23:
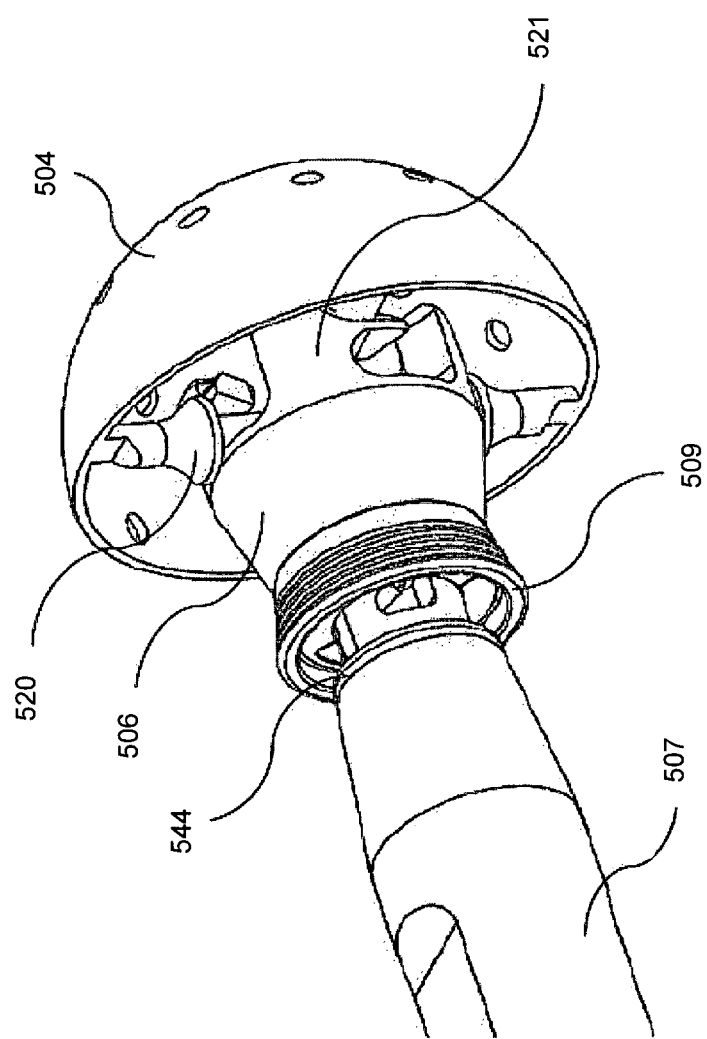
FIG. 23 shows a perspective view of the preferred embodiment of the reamer driver head having an acetabular reamer connected to it.

FIG. 23 shows the acetabular reamer 504 connected to the reamer driver 501. At least one connecting bar 505 is engaged into one L-shaped opening 531 of the driver head 506. When the acetabular reamer has spaced apart connecting bars, the more distal connecting bar is in contact with the front surface 532 of the driver head 506 (shown in FIG. 24). Centering features 520 may be used to keep the acetabular reamer 504 centered with the cylindrical portion 521 of the reamer head 506.

Figure 26A:
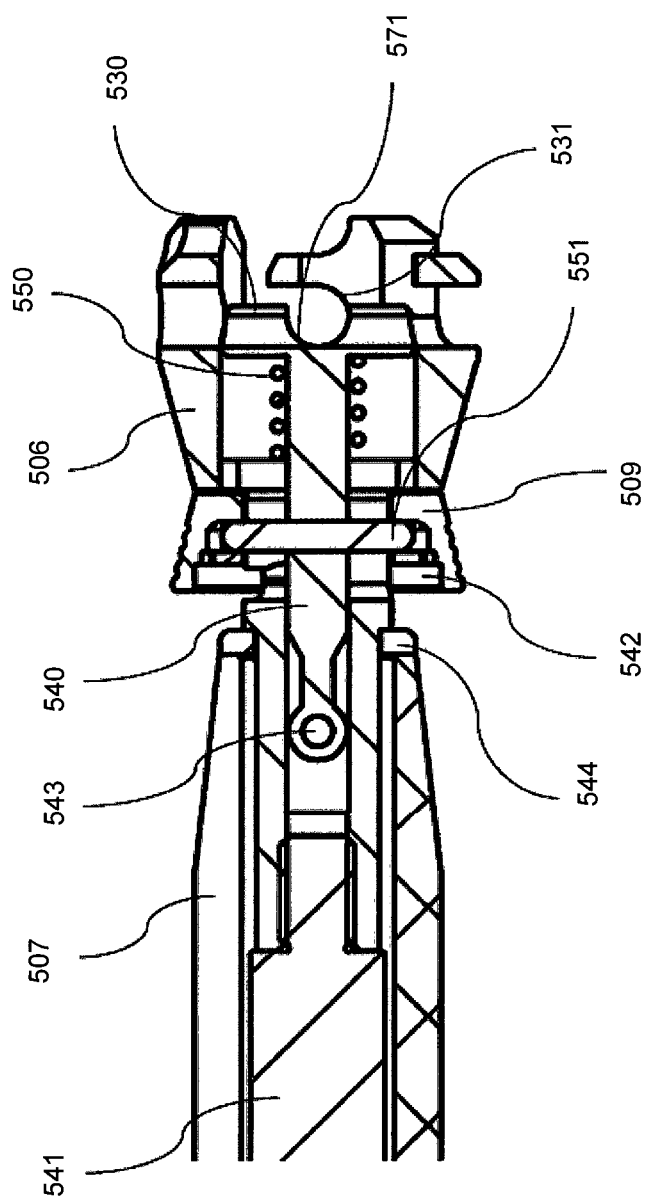
FIG. 26A shows a detailed cross-section view of the reamer driver head in its closed position.
Figure 26B:
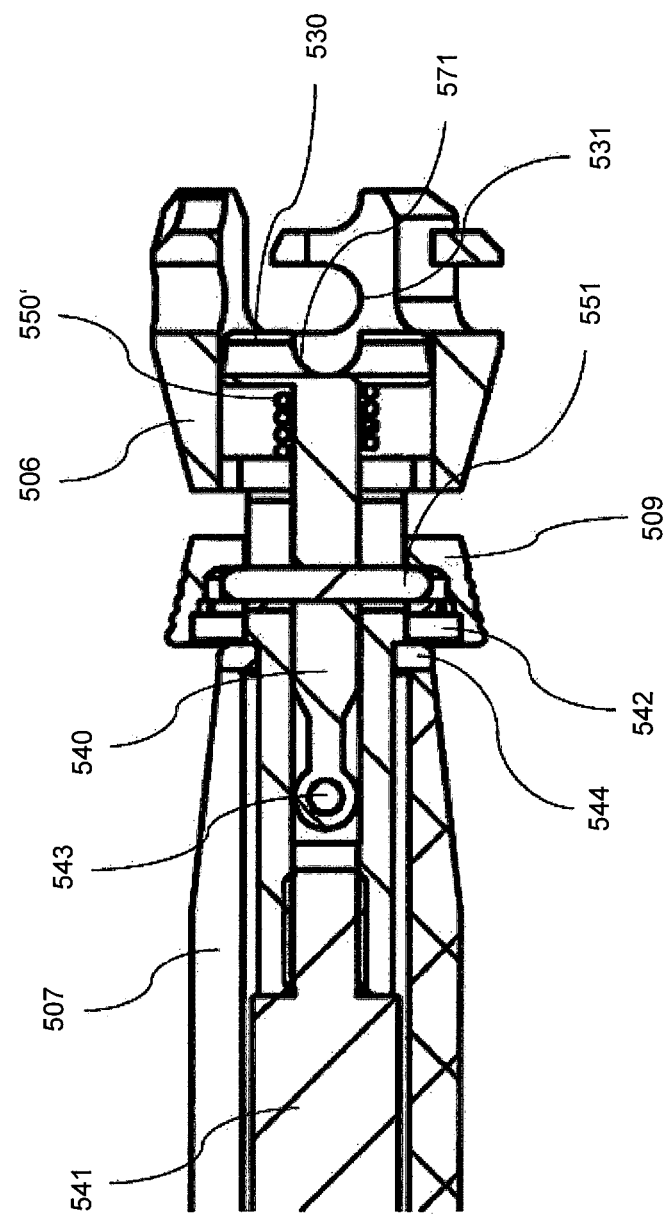
FIG. 26B shows a detailed cross-section view of the reamer driver head in its opened position.

Now referring to FIG. 25, a cross-section of the reamer driver 501 is shown. A locking member 540 is sliding in the center of the driver head 6 and shown in its locked position. The locking member 540 and its locking head 530 is capturing the connecting bar 505 of the acetabular reamer 504 once engaged into the L-shaped openings 531 and therefore maintaining the reamer firmly connected to the driver. FIG. 26A shows a different cross-section, perpendicular to the cross-section of FIG. 25. The locking member 540 is still in its locked position. At least one groove 571, located in the locking head 530, closes the L-shape opening 531 and maintains the connecting bar of the acetabular reamer in the connected position. A compression spring 550 maintains the locking member 540 in its locked position. A cross-pin 551, rigidly assembled into the locking member 540, can be inserted and connected into the release sleeve 509 and maintained in position by a spring washer 542. By pulling the release sleeve 509 backward, the locking member 540 and its locking head 530 move backward and clear the L-shaped opening 531, allowing the connecting bar of the acetabular reamer to come out, as shown in the cross-section view of FIG. 26B. In this opened position, the spring 550' is compressed. The acetabular reamer may also be connected to the reamer driver without having to manually pull on the release sleeve 509. While engaging the connecting bar into the L-shaped openings 531, the connecting bar contacts the front face of the locking head 530 and therefore pushes it backward until it reaches its opened position. This clears the L-shaped opening 531 and allows the connecting bar to be fully engaged into the L-shaped opening. Once the connecting bar is fully engaged into the L-shaped openings, the locking head 530 is pushed back by the compression spring 550 in its initial position. The grooves 571, located in the locking head 530, close the L-shape openings 531 and block the connecting bar of the acetabular reamer in the connected position. Pulling on the release sleeve 509 to release the connecting bar is mandatory.

Figure 27A:
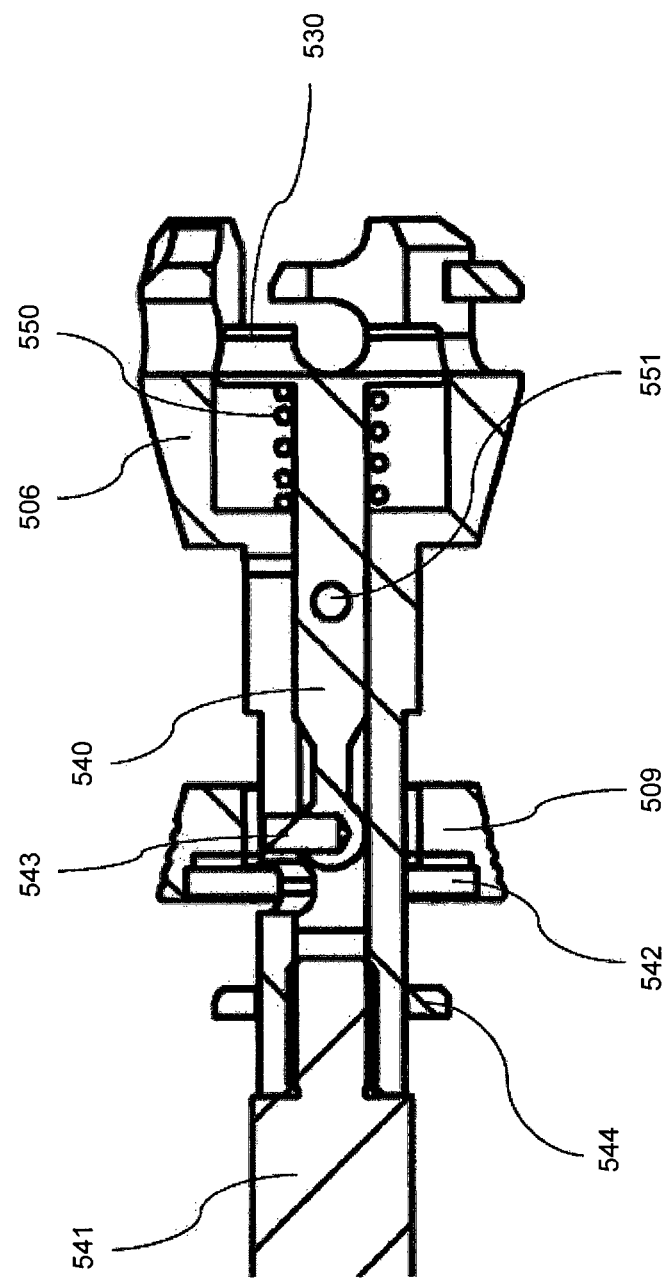
FIG. 27A shows a cross-section view of the reamer driver head partially disassembled.
Figure 27B:
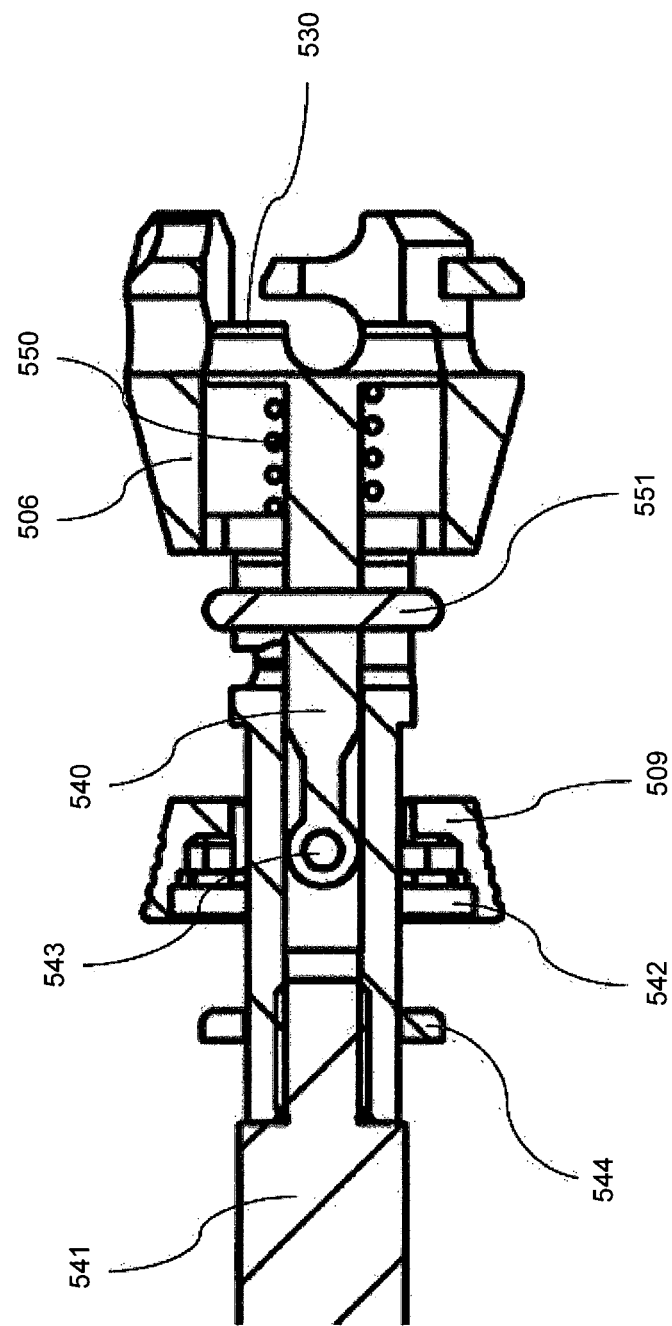
FIG. 27B shows a different cross-section view of the reamer driver head partially disassembled.

One advantage of the present invention is the ability of disassembling the reamer driver for cleaning and sterilization. FIGS. 27A and 27B show cross-section views of the reamer driver where the release sleeve 509 has been disconnected from the cross-pin 551. By rotating the release sleeve 509, the spring washer 542 allows disengagement of the cross-pin 551 and therefore disconnection of the two components. The handle sleeve 507 may also be pulled out of the elongated shaft 541 for better cleaning. The inside diameter of the washer 544 is adjusted in order to stay free on the shaft portion of the driver head 6 but not fall out of the assembly.

Figure 28A:
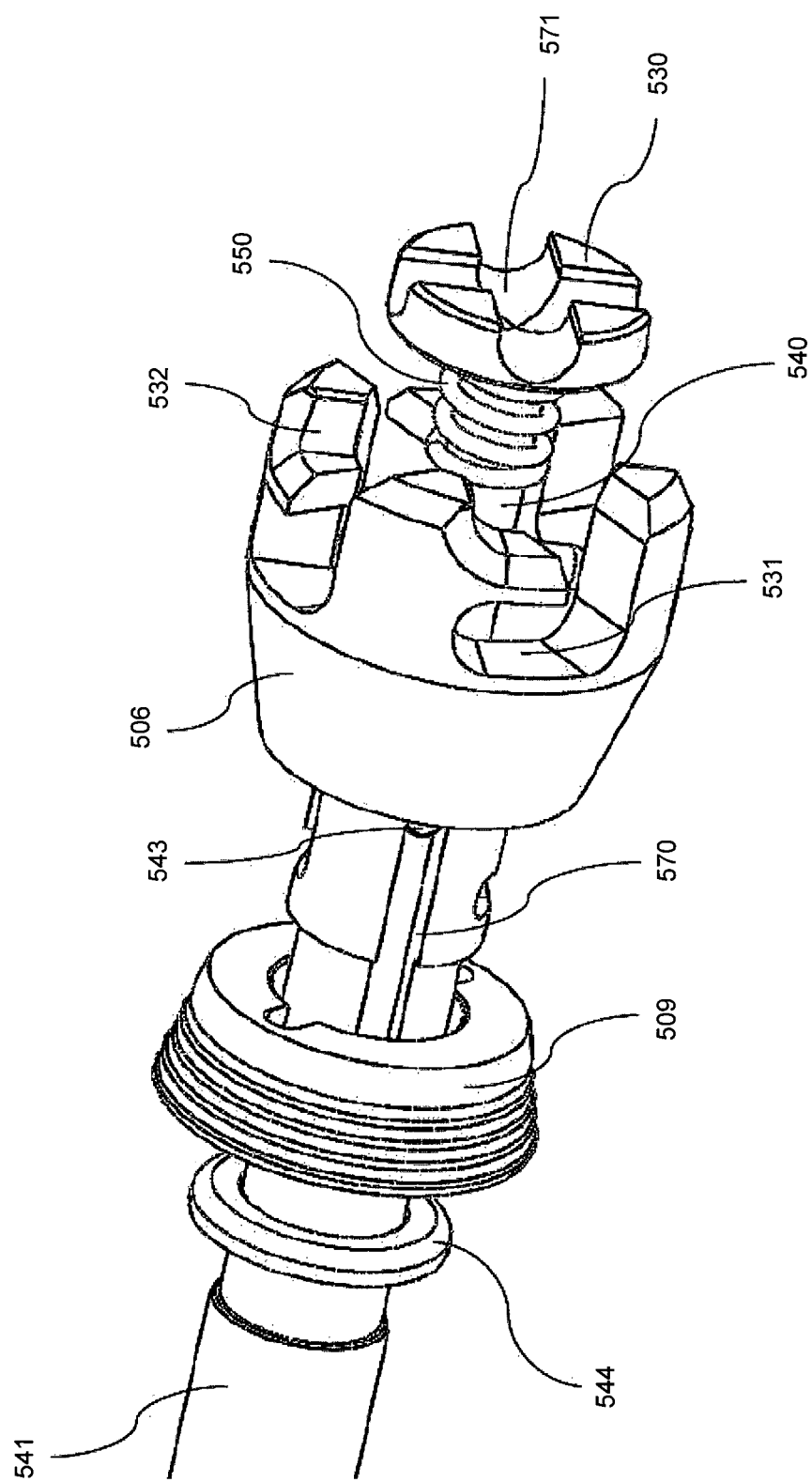
FIG. 28A shows a perspective view of the reamer driver head fully disassembled.
Figure 28B:
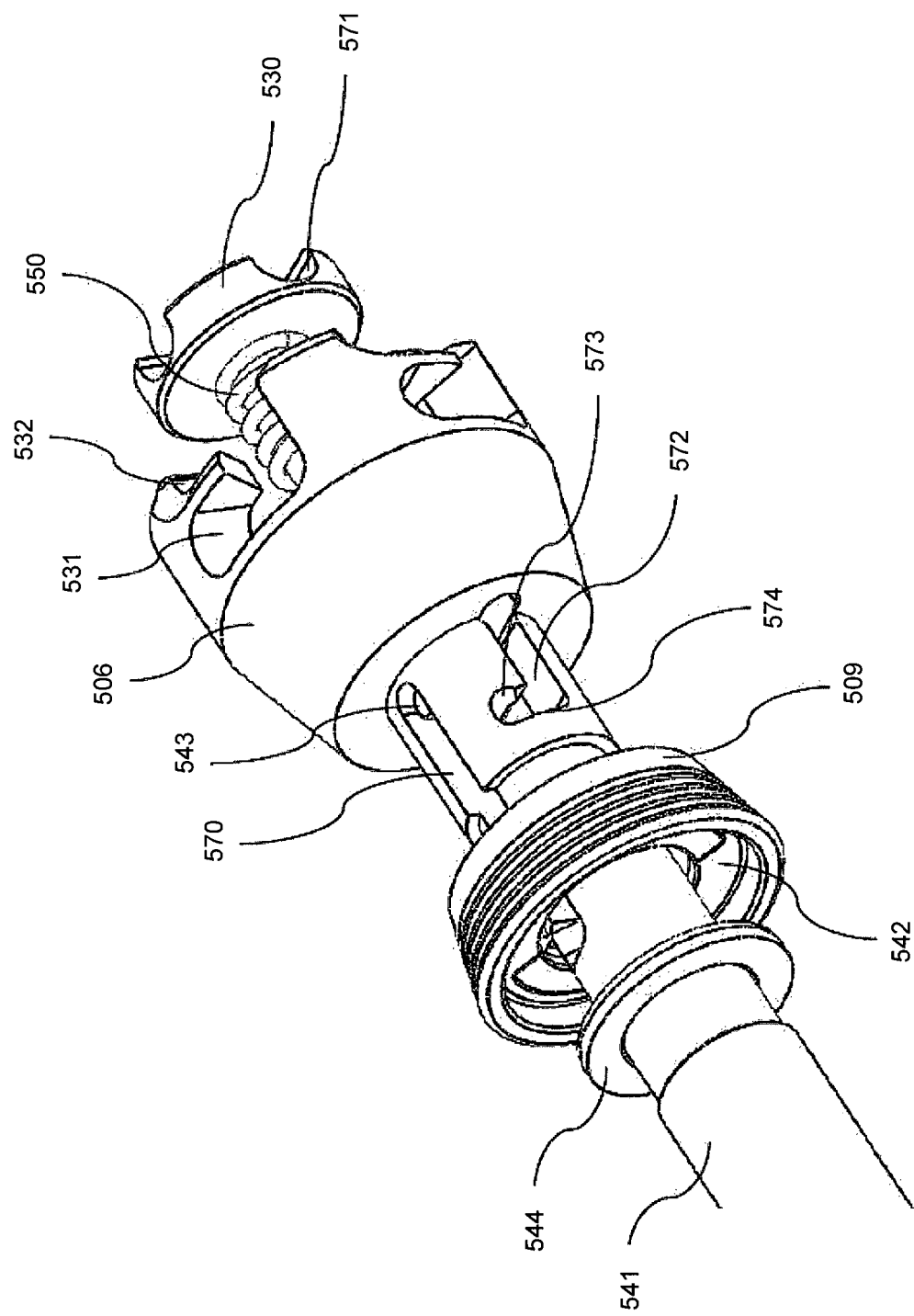
FIG. 28B shows a different perspective view of the reamer driver head fully disassembled.

Referring to FIGS. 28A and 28B, the fully disassembled reamer driver is shown. The release sleeve 509 has been disconnected from the cross-pin 551 allowing the locking member 540 and its locking head 530 to freely moves frontward and outside the driver head 506. A retaining pin 543 is connected to the proximal end of the locking member 540. This pin is captured into and slides in the groove 570 of the shaft portion of the driver head 506 and stops the locking member 540 to completely fall out of the reamer driver. This prevents the medical staff to lose any components during disassembling, cleaning and sterilization.

The groove 572 guides and limits the range of motion of the cross-pin 551, and therefore the movements of the release sleeve 509 when connected to it. By pulling the release sleeve 509 backward, the cross-pin 551 slide in the groove 572 until reaching its proximal end 574. The locking head 530 is then in its fully opened position and an acetabular reamer can be inserted into or pulled out of the driver head. If the release sleeve 509 is released from this position, the compression spring 550 will push the locking member 540 and its locking head 530 back in its initial closed position. When the locking member 540 and its locking head 530 are in the fully opened position, a counterclockwise rotation of the release sleeve 509 moves the cross-pin 551 towards the L-shaped end 573 of the groove 572. This position prevents the compression spring 550 to push the locking member 540 and its locking head 530 back in the closed position and therefore maintains the locking mechanism open. This option gives the surgeon the ability to use the reamer driver in the opened position without locking the acetabular reamer to the driver.

Figure 28C:
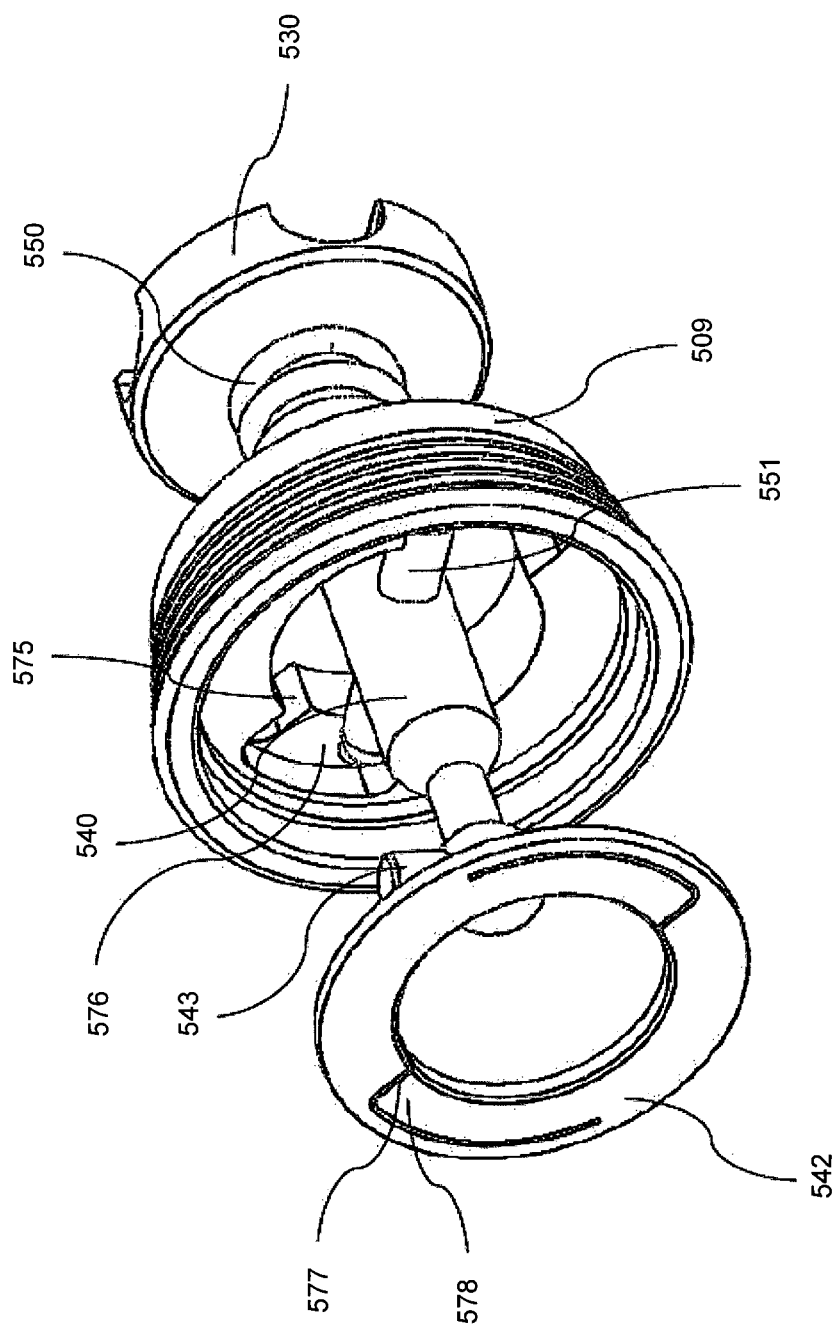
FIG. 28C shows an exploded view of the release sleeve and the locking mechanism.

FIG. 28C shows an exploded view of the release sleeve 509. It's worth noting that some of the components are not shown in this figure for clarity and simplification of the drawing. The opening 575 of the release sleeve 509 allows the cross-pin 551 to be inserted into it. The spring washer 542 has a groove 577 forming an elastic blade 578 acting as a spring. After insertion of the cross-pin 551 through the opening 575, a rotation of the release sleeve 509 clockwise locks the cross-pin 551 into the channel 576. The elastic blade 578 maintains pressure on the cross-pin 551 and avoids free motion of it. The release sleeve 509 is then connected to the cross-pin 551. For disassembling, a counterclockwise rotation of the release sleeve 509 disengages the cross-pin 551 from the channel 576. Disconnection force may be adjusted by modifying the dimensions of the groove 577 forming the elastic blade 578. Different geometries of the release sleeve and the spring washer allowing connection and disconnection of the cross-pin may be considered without changing the scope of the present invention. In a different embodiment, a spring loaded ball may be used in place of the spring washer. In a still different embodiment, release sleeve having forceps feature may be used to connect and disconnect the cross-pin.

Figure 29:
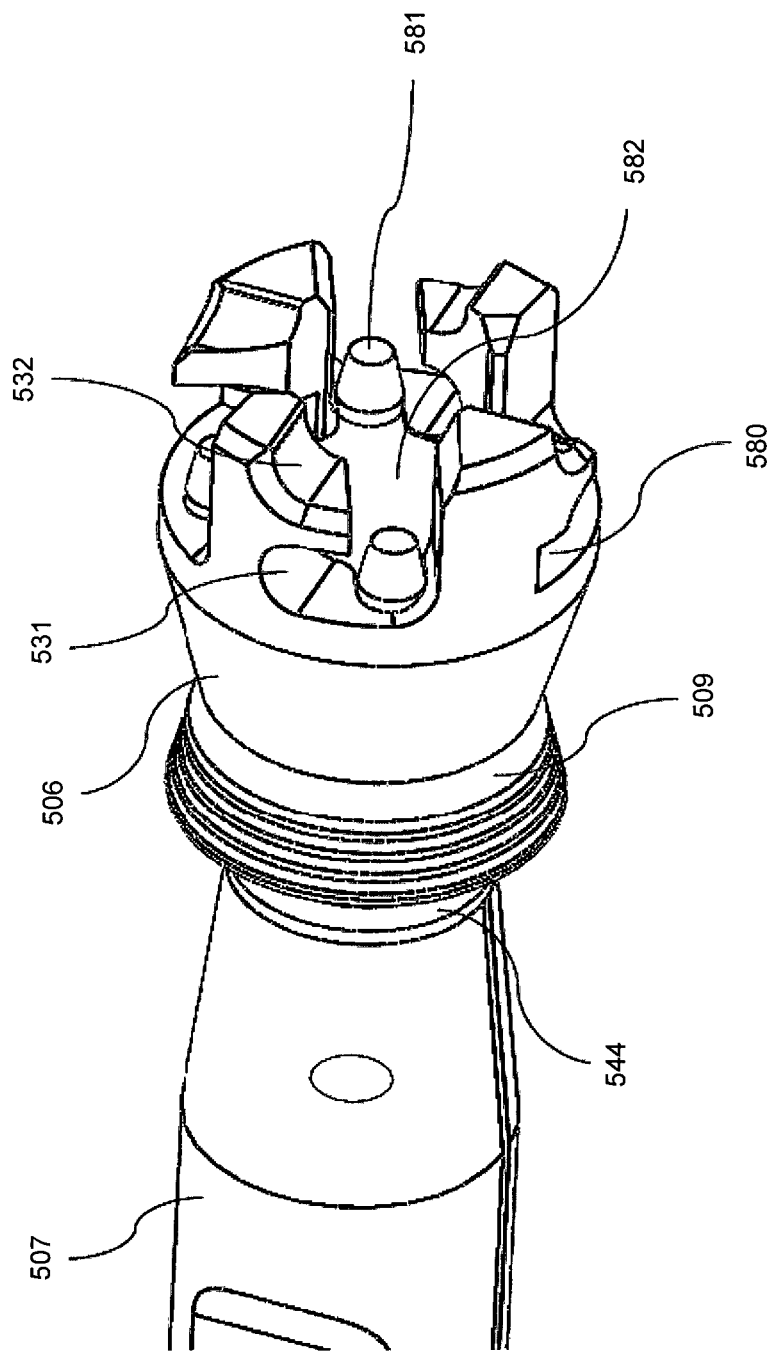
FIG. 29 shows a perspective view of a second embodiment of the reamer driver head.

Now referring to FIG. 29, a second embodiment of the reamer driver is shown. The locking head 582 has at least one pin 581 located in such a way to close the L-shaped openings 531 and therefore capture the connecting bars of the acetabular reamer once engaged into it in order to maintaining the reamer firmly connected to the driver. Different L-shaped openings 580 may be used to connect non-cylindrical connecting bars of different types of acetabular reamers. As shown is this figure, both rectangular L-shaped openings 580 and cylindrical L-shaped openings 531 are used in the same reamer driver in order to connect different acetabular reamers having either rectangular or cylindrical connecting bars.

Figure 30A:
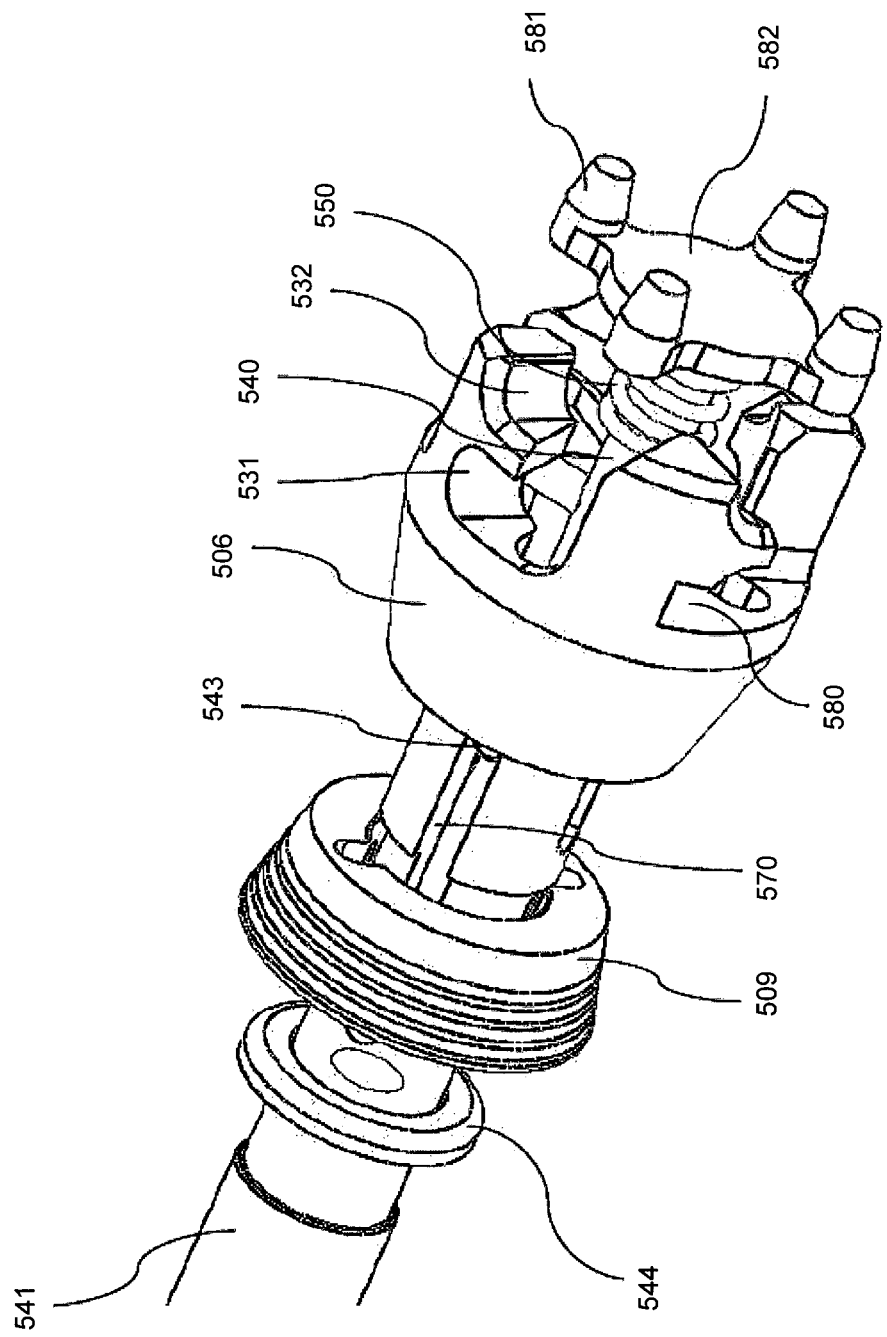
FIG. 30A shows a perspective view of a second embodiment of the reamer driver head fully disassembled.
Figure 30B:
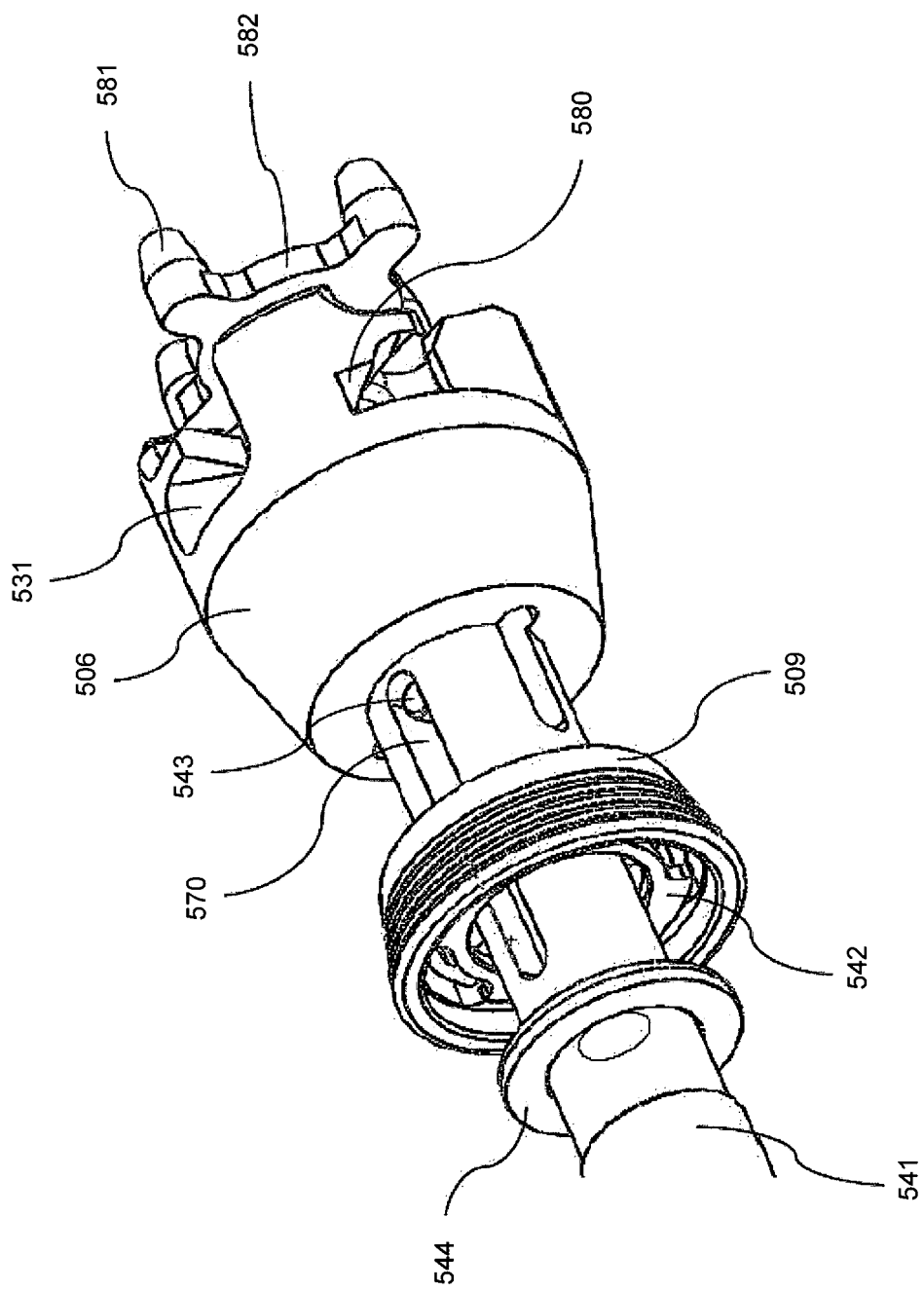
FIG. 30B shows a different perspective view of a second embodiment of the reamer driver head fully disassembled.

Referring to FIGS. 30A and 30B, the fully disassembled second embodiment of the reamer driver is shown. The release sleeve 509 has been disconnected from the cross-pin allowing the locking member 540 and its locking head 530 to freely moves frontward and outside the driver head 506. A retaining pin 543 is connected to the proximal end of the locking member 540. This pin is captured into and slides in the groove 570 of the shaft portion of the driver head 506 and stops the locking member 540 to completely fall out of the reamer driver.

Figure 31:
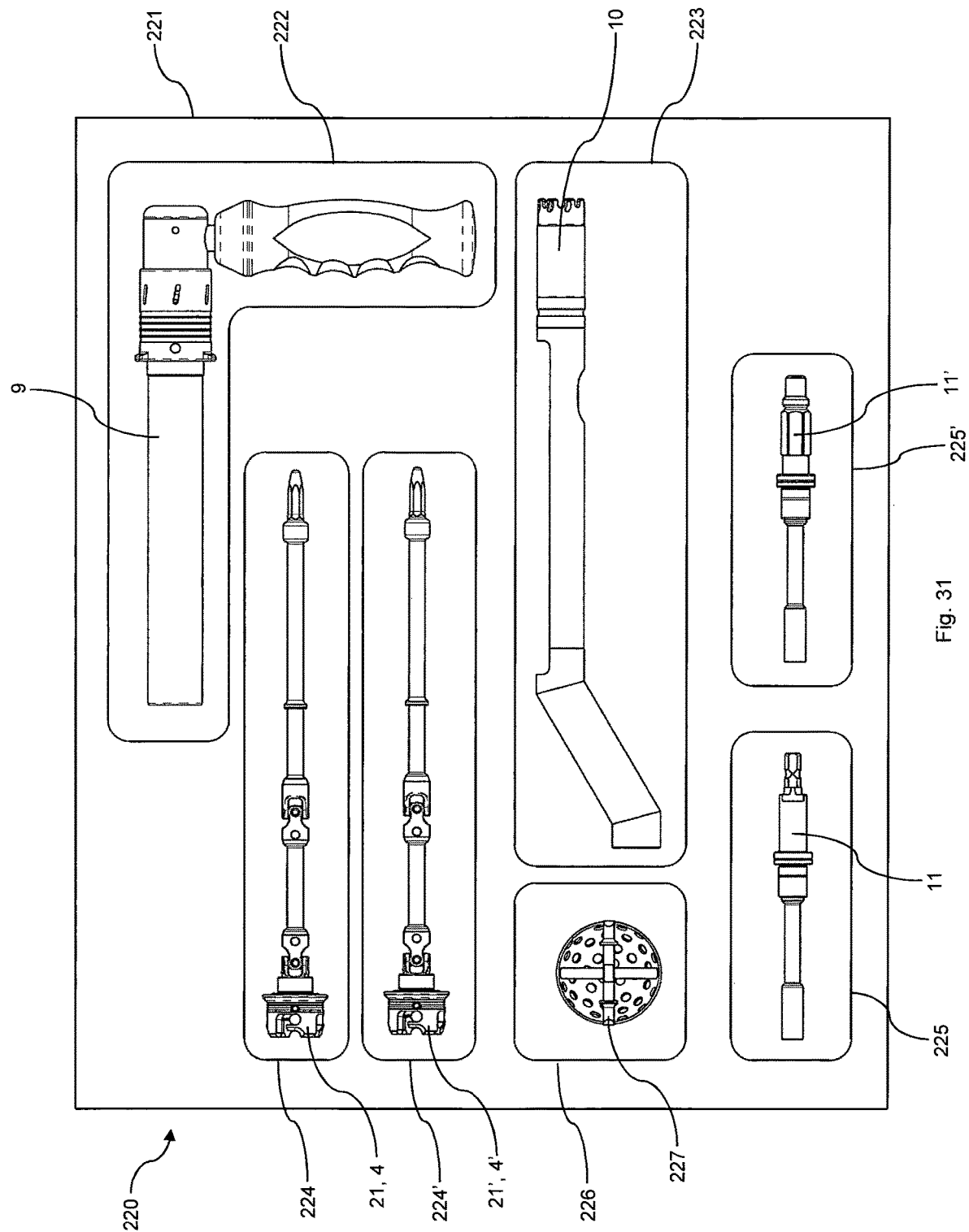
FIG. 31—is a kit of the invention.

Referring now to FIG. 31, a kit 220 includes the surgical reamer driver and its components (including some alternate components for alternate configurations), and in addition, a case 221 for organizing and storing the components of the kit. The surgical kit 220 further includes surgical tools 227 (one shown here by duplicates and others having differing outside diameters may be provided) of various sizes and styles, adapted to interface with the surgical tool connector 4. Optionally, an alternative motor coupling 11, 11' are provided, having an alternative connection configuration. Optionally, alternate transmission drive trains 21 and 21' are provided as well, each having an alternate surgical tool connector 4, 4'.

Figure 32:
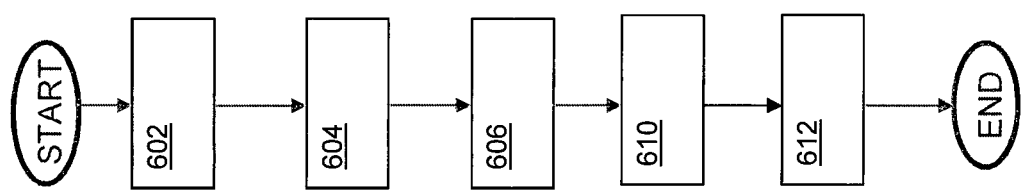
FIG. 32 is a flow chart of the method of the invention.

Referring now to FIG. 32, the method 600 of the invention includes several steps. In a first step 602, the sliding release sleeve 8 is actuated to unlock a handle assembly 9 from a housing 10, thereby permitting the de-encapsulation of a drive train 21 within the housing assembly. In a second step

604, the handle assembly is slid off of the housing thereby effectively de-encapsulating the drive train. In a third step 606, the motor shaft coupling 11 is pulled out of the housing thereby freeing the drive train from axial constraint on one end. In a fourth step 610, the drive train is unsnapped on the one end from a restraint 32 and lifted out of the housing thereby permitting removal of the drive train. In a fifth step 612, the drive train is pulled out of the housing, thus removing the drive train from the housing. Once disassembled, the components may be replaced with alternate components meeting another need or simply cleaned and/or sterilized in preparation for the next use.

An advantage of the present invention is to provide a reamer driver having fully closed tube in order to avoid penetration of debris and abrasion of soft tissues during use. The reamer driver shown in this application has only 4 components that can be easily replaced when worn out.

Another advantage is that the transmission of the load applied on the motor shaft coupling is transmitted to the body of the reamer handle only. The load applied on the handle is also transmitted to the body of the reamer handle only. There is no contact between the motor shaft coupling and the handle assembly. These two cumulated loads are directly transmitted to the reamer head without compressing the universal transmission drive chain, which only transmit the torque applied on the motor shaft coupling.

An advantage of the present invention is to provide a simple reamer driver connection that allows for the quick connect of different type of acetabular reamers from the center of the driver. In comparison to the existing reamer driver connections described in the prior art, the locking mechanism located in the center of the driver prevent debris and bone chips to enter into the mechanism and potentially disconnect the reamer from the reamer driver. It also reduces soft tissue irritation while rotating by limiting the sharp edges of components located around the head of the reamer driver.

In another advantage, the invention provides a locking mechanism in the head of a driver which, unlike the standard lock/release function, can be locked in its open position. This allows the surgeon to insert the cutting tool through a minimal invasive opening first. Then, once locked, the reamer handle can be inserted through the same minimal invasive opening and connected to the cutting tool without activating the locking of the mechanism.

Another advantage of the invention is to provide an easy to assemble and disassemble reamer driver connection for better cleaning and sterilization. The number of components and the risk that parts could be lost have been minimized.

It will be understood that the particular method and devices embodying the invention are shown by way of illustration and not as a limitation of the invention. Although certain illustrative embodiments of the invention have been shown and described here, a wide range of modification, changes and substitutions is contemplated in the foregoing disclosure.

Further, the invention should be considered as comprising all possible combinations of every feature described in the instant specification, appended claims, and/or drawing figures which may be considered new, inventive and industrially applicable.

It should be appreciated that the particular implementations shown and herein described are representative of the invention and its best mode and are not intended to limit the scope of the present invention in any way.

As will be appreciated by skilled artisans, the present invention may be embodied as a system, a device, or a method.

The present invention is described herein with reference to block diagrams, devices, components, and modules, according to various aspects of the invention. It will be understood that each functional block of the blocks diagrams, and combinations of functional blocks in the block diagrams, can be implemented by computer program instructions which may be loaded onto a general purpose computer, special purpose computer, or other programmable data processing apparatus to produce a machine, such that the instructions which execute on the computer or other programmable data processing apparatus create enable the functionality specified in the block diagrams.

Moreover, the system contemplates the use, sale and/or distribution of any goods, services or information having similar functionality described herein.

The specification and figures should be considered in an illustrative manner, rather than a restrictive one and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "includes", "comprising", or variations thereof, are intended to refer to a non-exclusive listing of elements, such that any apparatus, process, method, article, or composition of the invention that includes a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification, inclusive of the appendix hereto and any computer program comprised therein.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A surgical reamer driver having at least four basic components and a distal and proximal end, the four components being:
    a housing assembly having at least a proximal opening and a distal opening,
    a handle assembly disposed over the housing assembly and disengageable from the housing assembly,
    a transmission drive chain enclosed in the housing assembly, passing through the distal opening, and having a surgical tool connector at the distal end thereof, and
    a motor shaft coupling passing through the proximal opening thereof, wherein the transmission drive chain and the motor shaft coupling make up a drive chain assembly and are slideably and removably engaged together via an interfacing connection permitting disengagement of the drive chain assembly into two independent subcomponents when disassembled, the interfacing connection being disposed between the motor shaft coupling and the surgical tool connector and encapsulated within the housing assembly,
    these basic disengageable components forming a driver which in a fully assembled state effectively prevents debris from access in the inner workings of the drive while permitting full disassembly for cleaning.

2. The driver of claim 1, wherein the motor shaft coupling rotatably connects while remaining axially slidable with the interfacing connection which is adapted to connect to a drive motor at a proximal end of thereof.

3. The surgical reamer driver of claim 1, wherein the reamer driver is constructed to transmit axial forces through the housing assembly and to apply these forces, preferably through a bearing, to the surgical tool connector such that the transmission drive chain is bypassed.

4. The surgical reamer driver of claim 1, wherein the surgical tool connector includes a quick connect mechanism located at the center of the driver for coupling with at least one surgical tool thereby preventing debris and bone chips from entering the driver and reducing snag points and sharp edges thereby reducing tissue irritation during use.

5. The surgical reamer driver of claim 4, wherein the surgical tool connector is adapted to interface with at least two surgical reamer interfaces.

6. The surgical reamer driver of claim 5, wherein the quick connect mechanism provides a position for locking in an open, unlocked position.

7. The surgical reamer driver of claim 1, wherein the interfacing connection is encapsulated within the central region of the housing assembly.

8. The driver of claim 1, wherein the transmission drive chain includes at least one universal joint having a bearing recess for receiving bearings which avoid direct metal to metal contact.

9. The surgical reamer driver of claim 8, wherein the at least one universal joint has two forks wherein each fork has two arms into each of which a bearing is mounted so as to reduce friction.

10. The surgical reamer of claim 9 wherein at least one fork can be temporarily split in half for assembling the bearings.

11. The surgical reamer driver of claim 1, wherein the driver has a quick connect mechanism which comprises a bayonet connection.

12. A surgical kit comprising the surgical reamer driver of claim 1 together with other components, the kit further comprising a case for organizing and storing the components of the kit.

13. The surgical kit of claim 12, further including:
    a. surgical tools of various sizes and styles, adapted to interface with the surgical tool connector;
    b. optionally, an alternative motor coupling having an alternative connection configuration; and
    c. optionally, an alternate transmission drive chain having an alternate surgical tool connector.

14. The driver of claim 1 further comprising a handle assembly disposed over the housing assembly and disengageable from the housing assembly.

15. The driver of claim 14, wherein the handle assembly is disposed over the housing assembly such that axial forces applied by the user to the motor shaft coupling are decoupled from the transmission drive chain and applied to the surgical tool connector through the housing assembly only and wherein the forces applied by a user to the handle assembly are decoupled from both the transmission drive chain and the motor shaft coupling and applied to the surgical tool connector through the housing assembly, preferably through a thrust bearing.

16. The driver of claim 14, wherein the handle assembly includes a smooth sheath which encapsulates the transmission drive chain and its interfacing connection within the housing assembly.

17. The surgical reamer driver of claim 16, wherein the sheath extends distally from the handle assembly encapsulating a housing component having a lateral opening on one side thereof permitting removal of the transmission drive chain for cleaning, and an opening on an opposite side thereof, allowing finger access to facilitate removable of the drive chain.

18. The surgical reamer driver of claim 17, wherein the handle assembly includes a smooth sheath which fully closes the lateral opening of the housing assembly.

19. The driver of claim 14, wherein the handle assembly is connected to the housing via an angular repositioning mechanism.

20. The driver of claim 14, wherein the handle assembly is constructed to allow axial thrust to be transmitted into the housing assembly and not into the transmission drive chain or the motor shaft coupling.

21. The driver of claim 14 further including a sliding release sleeve mounted on the handle assembly, the sliding release sleeve comprising a lock/unlock mechanism allowing the handle assembly to be assembled or disassembled from the housing assembly, respectively.

22. The surgical reamer driver of claim 21, wherein the housing assembly has a slotted end in which slots an annular locking feature, such as pins of the handle assembly, engages and which locks a handle of the handle assembly in a selected angular position.

23. The surgical reamer driver of claim 22, wherein a retainer retains the housing assembly with the handle assembly so as to prevent it from freely removing during disassembly.

24. The surgical reamer driver of claim 23, wherein the retainer comprises at least one slot formed so that the slot is smaller than an interfacing diameter of the angular locking feature, preferably a pin, and wherein, a side wall of such slot may be elastically biased to expand an opening of the slot to capture the angular locking feature.

25. A surgical reamer driver having a proximal end comprising a motor shaft coupling, a distal end comprising a surgical tool connector having a release sleeve for disconnecting the surgical tool, the surgical tool connector further including a quick connect mechanism adapted for coupling with at least one surgical tool, such quick connect mechanism being located at the center of the driver and having an axial thickness of a given dimension greater than an axial activation distance of the quick connect mechanism between an unlock and lock position, this thickness being substantially embedded in the driver in the unlock position and then being exposed as it extends axially outwardly an amount less than the given dimension in the lock position thereby preventing the exposure of a seam or opening during activation, thus preventing debris and/or bone chips from entering the driver, wherein further, optionally, the release sleeve can be temporarily disconnected from the quick connect mechanism in order to pull it outside the driver head for cleaning, and wherein further a drive chain assembly made up of a transmission drive chain and a motor shaft coupling is slideably and removably engaged together via an interfacing connection permitting disengagement of the drive chain assembly into two independent subcomponents when disassembled, the interfacing connection being disposed between the motor shaft coupling and the surgical tool connector and encapsulated within the housing assembly.

* * * * *